US 8,012,703 B2

Sep. 6, 2011

(12) United States Patent
Hoeffler et al.

(10) Patent No.: US 8,012,703 B2
(45) Date of Patent: Sep. 6, 2011

(54) MICROARRAYS AND USES THEREFOR

(75) Inventors: James Hoeffler, Carlsbad, CA (US);
Joseph Fernandez, Carlsbad, CA (US);
Marc Nasoff, San Diego, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/490,069

(22) Filed: Jun. 23, 2009

(65) Prior Publication Data
US 2010/0022407 A1 Jan. 28, 2010

Related U.S. Application Data

(60) Continuation of application No. 10/035,368, filed on Oct. 26, 2001, now abandoned, which is a division of application No. 09/245,615, filed on Feb. 4, 1999, now Pat. No. 7,794,946.

(60) Provisional application No. 60/073,605, filed on Feb. 4, 1998.

(51) Int. Cl.
*G01N 31/00* (2006.01)
*G01N 33/53* (2006.01)

(52) U.S. Cl. ............ 435/7.21; 435/7.1; 436/1; 436/501; 436/518; 424/9.1; 424/520; 422/1; 422/50; 530/300; 530/350

(58) Field of Classification Search .................. None
See application file for complete search history.

(56) References Cited

U.S. PATENT DOCUMENTS

| | | | |
|---|---|---|---|
| 4,071,409 A | | 1/1978 | Messing et al. |
| 4,281,061 A | * | 7/1981 | Zuk et al. ................ 435/7.9 |
| 4,444,879 A | | 4/1984 | Foster et al. |
| 4,483,929 A | | 11/1984 | Szoka |
| 4,514,508 A | | 4/1985 | Hirschfeld |
| 4,562,157 A | | 12/1985 | Lowe et al. |
| 4,591,570 A | | 5/1986 | Chang |
| 4,690,715 A | | 9/1987 | Allara et al. |
| 4,722,896 A | | 2/1988 | Kadish |
| 4,728,591 A | | 3/1988 | Clark et al. |
| 4,802,951 A | | 2/1989 | Clark et al. |
| 4,816,567 A | | 3/1989 | Cabilly et al. |
| 4,865,998 A | | 9/1989 | Feickert et al. |
| 4,894,146 A | | 1/1990 | Giddings |
| 4,908,112 A | | 3/1990 | Pace |
| 4,973,493 A | | 11/1990 | Guire |
| 4,987,032 A | | 1/1991 | Miyasaka et al. |
| 4,994,373 A | | 2/1991 | Stavrianopoulos et al. |
| 5,075,077 A | | 12/1991 | Durley et al. |
| 5,079,600 A | | 1/1992 | Schnur et al. |
| 5,096,807 A | | 3/1992 | Leaback |
| 5,143,854 A | | 9/1992 | Pirrung et al. |
| 5,154,808 A | | 10/1992 | Miyasaka et al. |
| 5,160,597 A | | 11/1992 | Colapicchioni et al. |
| 5,242,828 A | | 9/1993 | Bergstrom et al. |
| 5,252,743 A | | 10/1993 | Barrett et al. |
| 5,270,167 A | | 12/1993 | Francoeur et al. |
| 5,281,540 A | | 1/1994 | Merkh et al. |
| 5,283,173 A | | 2/1994 | Fields et al. |
| 5,283,283 A | | 2/1994 | Ogata |
| 5,294,369 A | | 3/1994 | Shigekawa et al. |
| 5,296,114 A | | 3/1994 | Manz et al. |
| 5,304,487 A | | 4/1994 | Wilding et al. |
| 5,342,692 A | | 8/1994 | Ribi |
| 5,348,886 A | | 9/1994 | Lee et al. |
| 5,376,252 A | | 12/1994 | Ekstrom et al. |
| 5,384,261 A | | 1/1995 | Winkler et al. |
| 5,384,263 A | | 1/1995 | Kauvar |
| 5,405,766 A | | 4/1995 | Kallury et al. |
| 5,405,783 A | | 4/1995 | Pirrung et al. |
| 5,412,087 A | | 5/1995 | McGall et al. |
| 5,424,186 A | | 6/1995 | Fodor et al. |
| 5,429,708 A | | 7/1995 | Linford et al. |
| 5,429,807 A | | 7/1995 | Matson et al. |
| 5,432,099 A | | 7/1995 | Ekins |
| 5,436,134 A | | 7/1995 | Haugland et al. |
| 5,441,876 A | | 8/1995 | Singh |
| 5,445,934 A | | 8/1995 | Fodor et al. |
| 5,466,589 A | | 11/1995 | Olinger et al. |
| 5,472,881 A | | 12/1995 | Beebe et al. |
| 5,489,678 A | | 2/1996 | Fodor et al. |
| 5,491,097 A | | 2/1996 | Ribi |
| 5,498,545 A | * | 3/1996 | Vestal ................ 436/47 |
| 5,506,121 A | | 4/1996 | Skerra et al. |
| 5,510,270 A | | 4/1996 | Fodor et al. |
| 5,512,131 A | | 4/1996 | Kumar et al. |
| 5,512,492 A | | 4/1996 | Herron et al. |
| 5,514,501 A | | 5/1996 | Tarlov |

(Continued)

FOREIGN PATENT DOCUMENTS

DE 3939973 6/1991

(Continued)

OTHER PUBLICATIONS

*Bangs Laboratories.Inc.*, Aug. 29, 1999, 1-16.

(Continued)

*Primary Examiner* — Lisa V Cook

(57) ABSTRACT

Methods of using microarrays to simplify analysis and characterization of genes and their function are provided. Such methods can be used to identify and characterize antibodies having binding affinity for a specific target antigen. A method of determining gene expression at the protein level by contacting an array of characterized or uncharacterized antibodies on a solid surface with one or more proteins and identifying the antibodies to which said protein(s) binds also is provided. This method can be used to compare the protein expression in two different populations of cells, such as normal cells and cancer cells or resting cells and stimulated cells. In addition, a method of determining gene expression at the protein level by contacting a microarray of nucleic acid samples derived from a variety of different sources with one or more nucleic acid probes then identifying the sample or samples to which the probe binds is provided.

13 Claims, 7 Drawing Sheets

U.S. PATENT DOCUMENTS

| | | |
|---|---|---|
| 5,516,635 A | 5/1996 | Ekins et al. |
| 5,520,787 A | 5/1996 | Hanagan et al. |
| 5,532,128 A | 7/1996 | Eggers et al. |
| 5,532,142 A | 7/1996 | Johnston et al. |
| 5,538,897 A | 7/1996 | Yates, III et al. |
| 5,541,070 A | 7/1996 | Kauvar |
| 5,545,531 A | 8/1996 | Rava et al. |
| 5,571,410 A | 11/1996 | Swedberg et al. |
| 5,580,733 A * | 12/1996 | Levis et al. .................. 435/6 |
| 5,585,069 A | 12/1996 | Zanzucchi et al. |
| 5,593,838 A | 1/1997 | Zanzucchi et al. |
| 5,594,111 A | 1/1997 | Stolowitz |
| 5,603,351 A | 2/1997 | Cherukuri et al. |
| 5,605,662 A * | 2/1997 | Heller et al. ................. 422/68.1 |
| 5,620,850 A | 4/1997 | Bamdad et al. |
| 5,622,826 A | 4/1997 | Varma |
| 5,623,055 A | 4/1997 | Stolowitz |
| 5,624,711 A | 4/1997 | Sundberg et al. |
| 5,627,369 A * | 5/1997 | Vestal et al. ................. 250/287 |
| 5,629,213 A | 5/1997 | Kornguth et al. |
| 5,635,358 A | 6/1997 | Wilding et al. |
| 5,637,469 A | 6/1997 | Wilding et al. |
| 5,643,948 A | 7/1997 | Driedger et al. |
| 5,648,470 A | 7/1997 | Stolowitz |
| 5,653,939 A | 8/1997 | Hollis et al. |
| 5,665,582 A | 9/1997 | Kausch et al. |
| 5,674,712 A | 10/1997 | Grandi et al. |
| 5,677,195 A | 10/1997 | Winkler et al. |
| 5,677,196 A | 10/1997 | Herron et al. |
| 5,681,484 A | 10/1997 | Zanzucchi et al. |
| 5,688,642 A | 11/1997 | Chrisey et al. |
| 5,700,642 A | 12/1997 | Monforte et al. |
| 5,719,060 A | 2/1998 | Hutchens et al. |
| 5,726,026 A | 3/1998 | Wilding et al. |
| 5,731,152 A | 3/1998 | Maracas et al. |
| 5,741,700 A | 4/1998 | Ershov et al. |
| 5,744,305 A | 4/1998 | Fodor et al. |
| 5,756,355 A | 5/1998 | Lang et al. |
| 5,763,170 A | 6/1998 | Raybuck |
| 5,763,263 A | 6/1998 | Dehlinger et al. |
| 5,766,908 A | 6/1998 | Klein et al. |
| 5,776,674 A | 7/1998 | Ulmer |
| 5,776,706 A | 7/1998 | Siiman et al. |
| 5,776,748 A | 7/1998 | Singhvi et al. |
| 5,807,522 A | 9/1998 | Brown et al. |
| 5,807,755 A | 9/1998 | Ekins |
| 5,814,565 A | 9/1998 | Reichert et al. |
| 5,821,063 A * | 10/1998 | Patterson et al. .................. 435/6 |
| 5,827,658 A | 10/1998 | Liang |
| 5,834,319 A | 11/1998 | Ekins |
| 5,837,551 A | 11/1998 | Ekins |
| 5,837,832 A | 11/1998 | Chee et al. |
| 5,840,300 A | 11/1998 | Williams et al. |
| 5,843,767 A | 12/1998 | Beattie |
| 5,851,840 A | 12/1998 | Sluka et al. |
| 5,854,018 A | 12/1998 | Hitzeman et al. |
| 5,858,188 A | 1/1999 | Soane et al. |
| 5,858,804 A | 1/1999 | Zanzucchi et al. |
| 5,861,242 A | 1/1999 | Chee et al. |
| 5,866,345 A | 2/1999 | Wilding et al. |
| 5,866,363 A | 2/1999 | Pieczenik |
| 5,874,219 A | 2/1999 | Rava et al. |
| 5,885,793 A | 3/1999 | Griffiths et al. |
| 5,905,024 A | 5/1999 | Mirzabekov et al. |
| 5,919,523 A | 7/1999 | Sundberg et al. |
| 5,922,594 A | 7/1999 | Lof.ang.s |
| 5,922,617 A | 7/1999 | Wang et al. |
| 5,925,552 A | 7/1999 | Keogh et al. |
| 5,928,880 A | 7/1999 | Wilding et al. |
| 5,942,443 A | 8/1999 | Parce et al. |
| 5,945,334 A | 8/1999 | Besemer et al. |
| 5,981,734 A | 11/1999 | Mirzabekov et al. |
| 6,001,607 A | 12/1999 | Tang et al. |
| 6,040,193 A | 3/2000 | Winkler et al. |
| 6,051,380 A | 4/2000 | Sosnowski et al. |
| 6,064,754 A | 5/2000 | Parekh et al. |
| 6,066,448 A | 5/2000 | Wohlstadter et al. |
| 6,083,763 A | 7/2000 | Balch |
| 6,087,102 A | 7/2000 | Chenchik et al. |
| 6,087,103 A | 7/2000 | Burmer |
| 6,090,545 A | 7/2000 | Wohlstadter et al. |
| 6,100,099 A | 8/2000 | Gordon et al. |
| 6,103,479 A | 8/2000 | Taylor |
| 6,107,059 A | 8/2000 | Hart |
| 6,110,426 A | 8/2000 | Shalon et al. |
| 6,121,048 A | 9/2000 | Zaffaroni et al. |
| 6,124,102 A | 9/2000 | Fodor et al. |
| 6,140,045 A | 10/2000 | Wohlstadter et al. |
| 6,190,908 B1 | 2/2001 | Kang et al. |
| 6,197,506 B1 | 3/2001 | Fodor et al. |
| 6,197,599 B1 | 3/2001 | Chin et al. |
| 6,225,047 B1 | 5/2001 | Hutchens et al. |
| 6,232,066 B1 | 5/2001 | Felder et al. |
| 6,303,344 B1 | 10/2001 | Patten et al. |
| 6,309,820 B1 | 10/2001 | Sparks et al. |
| 6,316,186 B1 | 11/2001 | Ekins |
| 6,329,209 B1 | 12/2001 | Wagner et al. |
| 6,346,413 B1 | 2/2002 | Fodor et al. |
| 6,350,369 B1 | 2/2002 | Lewis et al. |
| 6,365,418 B1 | 4/2002 | Wagner et al. |
| 6,391,625 B1 | 5/2002 | Park et al. |
| 6,399,365 B2 | 6/2002 | Besemer et al. |
| 6,403,320 B1 | 6/2002 | Read et al. |
| 6,406,840 B1 | 6/2002 | Li et al. |
| 6,406,921 B1 | 6/2002 | Wagner et al. |
| 6,416,952 B1 | 7/2002 | Pirrung et al. |
| 6,440,662 B1 | 8/2002 | Gerwen et al. |
| 6,454,924 B2 | 9/2002 | Jedrzejewski et al. |
| 6,475,808 B1 | 11/2002 | Wagner et al. |
| 6,475,809 B1 | 11/2002 | Wagner et al. |
| 6,476,215 B1 | 11/2002 | Okamoto et al. |
| 6,531,283 B1 | 3/2003 | Kingsmore et al. |
| 6,544,739 B1 | 4/2003 | Fodor et al. |
| 6,565,045 B1 | 5/2003 | Correge et al. |
| 6,576,478 B1 | 6/2003 | Wagner et al. |
| 6,582,969 B1 | 6/2003 | Wagner et al. |
| 6,596,545 B1 | 7/2003 | Wagner et al. |
| 6,600,031 B1 | 7/2003 | Fodor et al. |
| 6,610,482 B1 | 8/2003 | Fodor et al. |
| 6,630,358 B1 | 10/2003 | Wagner et al. |
| 6,635,311 B1 | 10/2003 | Mirkin et al. |
| 6,682,942 B1 | 1/2004 | Wagner et al. |
| 6,692,751 B1 | 2/2004 | Zebedee et al. |
| 6,699,665 B1 | 3/2004 | Kim et al. |
| 6,720,157 B2 | 4/2004 | Indermuhle et al. |
| 6,780,582 B1 | 8/2004 | Wagner et al. |
| 6,790,940 B1 | 9/2004 | Zentgraf et al. |
| 6,897,073 B2 | 5/2005 | Wagner et al. |
| 6,899,137 B2 | 5/2005 | Unger et al. |
| 6,919,211 B1 | 7/2005 | Fodor |
| 6,943,034 B1 | 9/2005 | Winkler et al. |
| 6,960,457 B1 | 11/2005 | Spudich et al. |
| 7,132,251 B1 | 11/2006 | Markman et al. |
| 7,393,632 B2 | 7/2008 | Cheo et al. |
| 7,354,721 B2 | 4/2009 | Tchaga |
| 7,794,946 B1 | 9/2010 | Hoeffler et al. |
| 2002/0007051 A1 | 1/2002 | Cheo et al. |
| 2002/0106702 A1 | 8/2002 | Wagner et al. |
| 2002/0110933 A1 | 8/2002 | Wagner et al. |
| 2002/0119579 A1 | 8/2002 | Wagner |
| 2002/0132272 A1 | 9/2002 | Wagner et al. |
| 2002/0164656 A1 | 11/2002 | Hoeffler et al. |
| 2003/0003599 A1 | 1/2003 | Wagner et al. |
| 2003/0017149 A1 | 1/2003 | Hoeffler et al. |
| 2003/0073811 A1 | 4/2003 | Kozlowski et al. |
| 2003/0207467 A1 | 11/2003 | Snyder et al. |
| 2004/0024151 A1 | 2/2004 | Becker et al. |
| 2004/0241751 A1 | 12/2004 | Wagner et al. |
| 2004/0248323 A1 | 12/2004 | Zhou et al. |
| 2005/0008674 A1 | 1/2005 | Wagner et al. |
| 2005/0014292 A1 | 1/2005 | Wagner et al. |
| 2005/0026215 A1 | 2/2005 | Predki et al. |
| 2005/0095646 A1 | 5/2005 | Sherman |
| 2005/0100947 A1 | 5/2005 | Wagner |
| 2005/0118665 A1 | 6/2005 | Zhou et al. |
| 2005/0182242 A1 | 8/2005 | Snyder et al. |
| 2005/0233473 A1 | 10/2005 | Cicero et al. |
| 2005/0244854 A1 | 11/2005 | Cahill et al. |
| 2006/0035387 A1 | 2/2006 | Wagner et al. |

FOREIGN PATENT DOCUMENTS

| | | |
|---|---|---|
| DE | 19543232 | 5/1997 |
| EP | 0404097 | 6/1990 |
| EP | 596421 | 5/1994 |
| EP | 619321 | 12/1994 |
| EP | 0664452 A2 | 7/1995 |
| EP | 0780423 A1 | 12/1996 |
| EP | 818467 | 1/1998 |
| EP | 972564 | 1/2000 |
| EP | 1086742 | 3/2001 |
| EP | 1965213 | 9/2008 |
| GB | 2099578 | 12/1982 |
| JP | 2272081 | 11/1990 |
| JP | 2003500928 | 2/1991 |
| JP | 6041183 | 2/1994 |
| JP | 07-084372 | 3/1995 |
| WO | WO-86/006170 | 10/1986 |
| WO | WO-89/04489 | 5/1989 |
| WO | WO-99/05144 | 5/1990 |
| WO | WO-91/16425 | 10/1991 |
| WO | WO-99/01047 | 1/1992 |
| WO | WO-92/10588 | 6/1992 |
| WO | WO-99/020791 | 11/1992 |
| WO | WO-93/12248 | 6/1993 |
| WO | WO-99/11161 | 6/1993 |
| WO | WO-99/19172 | 9/1993 |
| WO | WO-95/08770 | 3/1995 |
| WO | WO-99/18377 | 7/1995 |
| WO | WO-99/35505 | 12/1995 |
| WO | WO-96/02830 | 2/1996 |
| WO | WO-96/29629 | 9/1996 |
| WO | WO-96/36436 | 11/1996 |
| WO | WO-96/38726 | 12/1996 |
| WO | WO-96/39937 | 12/1996 |
| WO | WO-99/10365 | 3/1997 |
| WO | WO-97/32017 | 9/1997 |
| WO | WO-97/33737 | 9/1997 |
| WO | WO-97/36681 | 10/1997 |
| WO | WO-97/41424 | 11/1997 |
| WO | WO-97/41425 | 11/1997 |
| WO | WO-97/42507 | 11/1997 |
| WO | WO-99/039481 | 3/1998 |
| WO | WO-98/23948 | 6/1998 |
| WO | WO-98/27229 | 6/1998 |
| WO | WO-98/43086 | 10/1998 |
| WO | WO-99/20749 | 10/1998 |
| WO | WO-98/50773 | 11/1998 |
| WO | WO-99/053103 | 11/1998 |
| WO | WO-98/59361 | 12/1998 |
| WO | WO-99/11777 | 3/1999 |
| WO | WO-99/28502 | 6/1999 |
| WO | WO-99/039210 | 8/1999 |
| WO | WO-99/40434 | 8/1999 |
| WO | WO-99/45130 | 9/1999 |
| WO | WO-99/57312 | 11/1999 |
| WO | WO-00/06770 | 2/2000 |
| WO | WO-00/07024 | 2/2000 |
| WO | WO-00/20475 | 4/2000 |

OTHER PUBLICATIONS

Abstract XP002291800, *Derwent Publications Ltd., London, GB; Class A89, AN 1997-011913*, 1997.
08155312.5, Office action mailed on Feb. 25, 2009.
U.S. Appl. No. 09/245,615, Amendment—After Non-Final Office Action mailed Dec. 8, 2006, U.S. Appl. No. 09/245,615, Dec. 8, 2006, 20.
U.S. Appl. No. 09/245,615, Amendment—After Non-Final Rejection mailed Jan. 18, 2005, U.S. Appl. No. 09/245,615, Jan. 18, 2005, 12.
U.S. Appl. No. 09/245,615, Amendment—After Non-Final Rejection mailed May 17, 2006, U.S. Appl. No. 09/245,615, May 17, 2006, 23.
U.S. Appl. No. 09/245,615, Amendment—After Non-Final Rejection mailed Dec. 18, 2007, U.S. Appl. No. 09/245,615, Dec. 18, 2007, 16.
U.S. Appl. No. 09/245,615, Amendment After Final mailed Oct. 21, 2005, U.S. Appl. No. 09/245,615, Oct. 21, 2005, 13.
U.S. Appl. No. 09/245,615, Final Office Action mailed Mar. 19, 2008, U.S. Appl. No. 09/245,615, Mar. 19, 2008, 17.
U.S. Appl. No. 09/245,615, Final Office Action mailed Apr. 21, 2005, U.S. Appl. No. 09/245,615, Apr. 21, 2005, 18.
U.S. Appl. No. 09/245,615, Non-Final Office Action mailed Mar. 17, 2009, 3.
U.S. Appl. No. 09/245,615, Non-Final Office Action mailed Jun. 18, 2007, U.S. Appl. No. 09/245,615, Jun. 18, 2007, 42.
Non-Final Office Action mailed Aug. 8, 2006, U.S. Appl. No. 09/245,615 Aug. 8, 2006, 24.
U.S. Appl. No. 09/245,615, Non-Final Office Action mailed Oct. 13, 2004, U.S. Appl. No. 09/245,615, Oct. 13, 2004, 14.
U.S. Appl. No. 09/245,615, Non-Final Office Action mailed Nov. 17, 2005, U.S. Appl. No. 09/245,615, Nov. 17, 2005, 15.
U.S. Appl. No. 09/245,615, Office Action mailed Dec. 11, 2009, 12.
U.S. Appl. No. 09/245,615, Requirement for Restriction/Election mailed Oct. 25, 2000, U.S. Appl. No. 09/245,615 Oct. 25, 2000, 24.
U.S. Appl. No. 09/245,615, Requirement for Restriction/Election mailed—Jun. 20, 2000, U.S. Appl. No. 09/245,615, Jun. 20, 2006, 6.
U.S. Appl. No. 09/245,615, Response to Election/Restriction mailed Apr. 26, 2004, U.S. Appl. No. 09/245,615, Apr. 26, 2004, 9.
U.S. Appl. No. 09/245,615, Response to Election / Restriction mailed Apr. 30, 2001, U.S. Appl. No. 09/245,615. Apr. 30, 2001, 11.
U.S. Appl. No. 09/245,615, Response to Election / Restriction mailed Jul. 26, 2000, U.S. Appl. No. 09/245,615, Jul. 26, 2000, 5.
09180044.1, Partial EP Search Report mailed on Apr. 26, 2010.
09245615, Notice of Allowance Mailed Jun. 23, 2010, 7.
U.S. Appl. No. 10/035,368, Non-Final Office Action mailed Dec. 23, 2008.
99905748.2, European Search Report mailed Dec. 27, 2004, 7.
99905748.2, Partial European Search Report mailed Sep. 6, 2004, 7.
Adams, Mark D. et al., "Complementary DNA Sequencing: Expressed Sequence Tags and Human Genome Project", *Science*, vol. 252, Jun. 21, 1991, 1651-1656.
Aguaus, Arthur P. et al., "Cross-Reactivity and Sequence Homology between the 65-Kilodalton Mycobacterial Heat Shock Protein and Human Lactoferrin, Transferrin, and DR(beta) Subsets of Major Histocompatibility Complex Class II Molecules.", *Infection and Immunity*, vol. 58, No. 5, May 1990, 1461-1470.
Ahluwalia, a et al., "A Comparative Study of Protein Immobilization Techniques for Optical Immunosensors", *Biosensors & Bioelectronics*, vol. 7, No. 3, 1992, 207-214.
Allen, Patrick et al., "Isolation of high-affinity RNA ligands to HIV-1 integrase from a random pool", *Virology*, vol. 209, No. 2, 1995, 327-336.
Arenkov, Pavel et al., "Protein Microchips: Use for Immunoassay and Enzymatic Reactions", *Analytical Biochemistry* vol. 2781 2000, 123-131.
Baecher-Allan, Clare M. et al., "Differential Epitope Expression of Ly-48 (Mouse Leukosialin)", *Immunogenetics*, vol. 37, No. 3, 1993, 183-192.
Becker, E. W. et al., "Fabrication of microstructures with high aspect ratios and great structural heights by synchrotron radiation lithography, galvanoforming, and plastic moulding (LIGA process)", *Microelectronic Engineering*, vol. 4, 1986, 35-56.
Becker, E. W. et al., "Production of separation-nozzle systems for uranium enrichment by a combination of x-ray lithography and galvanoplastics", *Naturwissenchaften*, vol. 69, 1982, 520-523.
Benoist, Christophe et al., "In vivo sequence requirements of the SV40 early promoter region", *Nature*, vol. 290, Mar. 26, 1981, 304-310.
Bernard, B., *Bulletin de la Societe de Chimie Biogigue*, vol. 41, 1959, 891-899.
Bhatia, Suresh K. et al., "Use of Thiol-Terminal Silanes and Heterobifunctional Crosslinkers for Immobilization of Antibodies on Silica Surfaces", *Analytical Biochemistry*, vol. 178, No. 2, 1989, 408-413.
Bielke, W et al., "Characterizatin of a Novel Murine Testis-Specific Serine/Threonine Kinase", *Gene*, vol. 139, No. 2, Feb. 25, 1994, 235-239.
Bieri, Christoph et al., "Micropatterned lmmobilzation of a G ProteinCoupled Receptor and Direct Detection of G Protein Activation", *Nat. Biotechnol*. vol. 17, No. 11, Nov. 1999, 1105-1108.

Binkley, Jonathan et al., "RNA ligands to human nerve growth factor", *Nucleic Acids Research*, vol. 23, N. 16, 1995, 3198-3205.

Blanc, Bernard, "Immunoelectrophoretic two-dimensional analysis in a jellified medium", *Bulletin de la Societe de Chimie Biologique*, vol. 41, (English Abstract only), 1959, 891-899.

Bollon and Stauver et al., "DNA Transformation Efficiency of Various Bacterial and Yeast Host-Vector Systems", Journal of Clinical Hematology and Oncology, vol. 10, No. 2, 1980, 39-48..

Botstein, David et al., "Making Mutations in Vitro and Putting Them Back Into Yeast", *Miami Winter Symposia*, vol. 19, 1982, 265-274.

Broach, James R., "The Yeast Plasmid 2u, Circle", *Cell* vol. 28, 1982, 203-204.

Brott, B. K. et al., "GTPase-Activating Protein Interactions with the Viral and Cellular Src Kinases", *Proceedings of the National Academy of Science*, vol. 88, Feb. 1991, 755-759.

Brunk, Clifford F. et al., "Comparison of various ultraviolet sources for fluorescent detection of ethidium bromide-DNA complexes in polyacrylamide gels.", *Analytical Biochemistry*, vol. 82, No. 2, Oct. 1977, 455-462.

Bussow, Konrad et al., "A Method for Global Protein Expression and Antibody Screening on High-Density Filters of an Arrayed cDNA Library", *Nucleic Acids Research*, vol. 26, No. 21, 1998, 5007-5008.

Cahill, Dolores J., "Protein and antibody arrays and their medical applications", *Journal of Immunological Methods*, vol. 250, No. 1-214/2001, 81-91.

Cano, R J. et al., "Detection of salmonellas by DNA hybridization with a fluorescent alkaline phosphatase substrate.", *Journal of Applied Bacteriology*, vol. 72, No. 5, May 1992, 393-399.

Cano, Raul J. et al., "DNA hybridization assay using Attophos, a fluorescent substrate for alkaline phosphatase.", *Biotechniques*, vol. 12, No. 2. Feb. 1992, 264-2693

Cariello, Neal F. et al., "DNA damage produced by ethidium bromide staining and exposure to ultraviolet light.", *Nucleic Acids Research*, vol. 16, No. 9, May 11, 1998, 4157.

Centatiempo, Y., "Prokaryotic gene expression in vitro: transcription-translation coupled systems", *Biochimie*, vol. 68, 1986, 505-515.

Cha, Hyung J. et al., "Expression of Fused Protein, Human Interleukin-2 Simplified asa Fusion with Green Flourescent Protein, in Suspended Sf-9 Insect Cells", *Journal of Biotechnology*, vol. 69, Nov. 1997, 9-17.

Chesnut, Jonathan D. et al., "Selective isolation of transiently transfected cells from a mammalian cell population with vectors expressing a membrane anchored single chain antibody", *Journal of immunological Methods*, vol. 193, No. 1, Jun. 14, 1996, 17-27.

Chong, Shaorong et al., "Single-col. purification of free recombinant proteins using a self-cleavable affinity tag derived from a protein splicing element", *Gene Elsevier Science B.V.*, vol. 192,1997, 271-281.

Chu et al., "Immunochemical Technology for Environmental Applications", *ACS Symposium Series*, vol. 657, 1997, 170-184.

Chu, F. W. et al., "Microarray-Based Immunoassays", *Am Chem Soc.-657*, 1997, 170-184.

Clackson, Tim et al., "Making Antibody Fragments Using Phage Display Libraries", *Nature*, vol. 352, 1991, 624-628.

Clark, Matthew D. et al., "Construction and analysis of arrayed cDNA libraries", *Methods in Enzymology*, vol. 303, 1999, 205-233.

Cload, Sharon T. et al., "Development of improved tRNAs for in vitro biosynthesis of proteins containing unnatural amino acids", *Chemistry and Biology*, vol. 3, No. 12, 1996, 1033-1038.

Cohen, Claudia B. et al., "A MicroChip-Based Enzyme Assay for Protein Kinase a", Analytical *Biochemistry*, vol. 273, Aug. 15, 1999, 89-97.

Collioud, Andre et al., "Oriented and covalent immobilization of target molecules to solid supports: Synthesis and application of a light-activatable and thiol-reactive cross-linking reagent", *Bioconjugate. Chem.*, vol. 4, No. 6, 1993, 528-536.

Condra, Jon H. et al., "In vivo emergence of HIV-1 variants resistant to multiple protease inhibitors", *Nature*, vol. 374, Apr. 6, 1995, 569-571.

Copeland, Connie S. et al., "Nuclear pore complex antigen delineate nuclear envelope dynamics in vegetative and conjugating Saccharomyces cerevisiae.", *Yeast*, vol. 9, No. 3, PMID: 8488725, 1993, 235-249.

Couchman, Grace M. et al., "p53lyn and p56lyn: A New Signaling Pathway in Human Endometrium and Endometrial Adenocarcionomas", *J. Soc. Gynecol Investig.*, vol. 4, No. 2, 1997, 103-109.

Cu Po, James F., "Electrophoretic Analysis of Nuclear Matrix Proteins and the Potential Clinical Applications", *Journal of Chromatography*, vol. 569, No. 1-2, 1991, 389-406.

Dammer, U et al., "Specific antigen/antibody interactions measured by force microscopy", *Biophysical Journal*, vol. 70, May 1996, 2437-2441.

Daniels, Dion A. et al., "Phage Peptide Libraries", *Methods: A Companion to Methods in Enzymology*, vol. 9, 1996, 494-507.

Davies, et al., "Generation of cDNA Expression Libraries Enriched for InFrame Sequences", *Proceedings of the National Academy of Sciences (PNAS)*, vol. 94, 1997, 2128-2132.

Dawson, Susan L. et al., "Peptide-Derived Self-Assembled Monolayers: Adsorption of N-Stearoyl I-Cysteine Methyl Ester on Gold", *Journal of Molecular Recognition*, vol. 10, 1997, 18-25.

Duschl, Claus et al., "Surface Engineering: Optimization of Antigen Presentation in Self-Assembled Monolayers", *Biophysical Journal*, vol. 70, Apr. 1996, 1985-1995.

Dzgoev, Anatoll et al., "Microformat Imaging ELISA for Pesticide Determination", *Analytical Chemistry*, vol. 68, No. 19, Oct. 1, 1996, 3364-3389.

Ekins, R. et al., "Developmentof Microspot Multi-Analyte Ratiometric Immunoassay Using Dual Fluorescent•Labelled Antibodies", *Analytica Chimica Acta*; vol. 227, 1989, 73-96.

Ekins, Roger P. et al., "Fluorescence Spectroscopy and its Application to a New Generation of High Sensitivity, Multi-Microspot, Multianalyte, Immunoassay", *Clinica Chimica Acta.*, vol. 194, No. 1, Dec. 17, 1990, 91-114.

Ekins, R. et al., "Immunoassay and other ligand assays: present status and future trends", *International Federation of Clinical Chemistry / IFCC*, vol. 9, No. 3, Sep. 1, 1997, 100, 102-109.

Ekins, Roger P., "Ligand Assays from Electrophoresis to Miniaturized Microarrays", *Clin. Chem.*, vol. 44, No. 9, 1998, 2015-2030.

Ekins, Roger P. et al., "Multianalyte Microspot Immunoassay. The Microanalytical compact Disk of the Future", *Ann Biol Clin*, vol. 50, 1992, 337-353.

Ellman, Jon et al., "Biosynthetic method for introducing unnatural amino acids site-specifically into proteins", *Methods in Enzymology*, vol. 202, 1991, 301-337.

Emili, Alia Q. et al., "Large Scale Functional Analysis Using Peptides or Protein Arrays", *Nature Biotechnology*, vol. 18, No. 4, Apr. 2000, 393-397.

EP08155312.5, European Search Report mailed on Jun. 16, 2009.

Freij-Larsson, C. et al., "Adsorption Behaviour of Amphiphilic Polymers at Hydrophobic Surfaces: Effects on Protein Adsorption", *Biomaterials*, vol. 17, No. 22, 1996, 2199-2207.

Ganz, Peter R. et al., "Characterization of Plasminogen Binding to Human Capillary and Arterial Endothelial Cells", *Biochem Cell Biol.*, vol. 69, No. 7 Jul. 1991,442-448.

Geoghegan, Kieran F. et al., "Fluorescence-Based Continuous Assay for the Aspartyl Protease of Human Immunodeficiency Virus-1", *FEBS*, vol. 262, No. 1, Mar. 1990, 119-122.

Gilman, Michael Z. et al., "Isolation of sigma-28-specific promoters from Bacillus subtilis DNA", *Gene Elsevier Science Publishers*, vol. 32, No. 1-2, Dec. 1984, 11-20.

Gold, L. et al., "Translational Initiation in Prokaryotes", *Ann. Rev. Microbiol.* Annual Reviews, Inc., vol. 35, 1981, 365-403.

Golding, Hana et al., "Identification of homologous regions in human immunodeficiency virus I gp41 and human MHC class II beta 1 domain. I. Monoclonal antibodies against the gp41-derived peptide and patients' sera react with native HLA class II antigens, suggesting a role . . .", *Journal of Experimental Medicine*, vol. 167, Mar. 1988, 914-923.

Gottesman, Susan et al., "Bacterial Regulation: Global Regulatory Networks", *Ann. Rev. Genet. Annual Reviews, Inc.*, vol. 18,1984, 415-441.

Gottlieb, Philip et al., "Binding Studies of SV40 T-antigen to SV40 binding site II", *Nucleic Acids Research* vol. 13, No. 18 Sep. 1985, 6621-6634.

Graundemann, Dirk et al., "Protection of DNA during preparative agarose gel electrophoresis against damage induced by ultraviolet light.", *Biotechniques*, vol. 21, No. 5 Nov. 1996, 898-903.

Hamer, Dean H. et al., "Regulation in Vivo of a Cloned Mammalian Gene: Cadmium Induces the Transcription of a Mouse Metallothionein Gene in SV40 Vectors", *Journal of Molecular and Applied Genetics*, vol. 1,1982, 273-288.

Hanks, Steven K. et al., "Protein kinases 6. The eukaryotic protein kinase superfamily: kinase (catalytic) domain structure and classification", *The FASEB Journal*, vol. 9 May 1995, 576-596.

Hartman, Zlata et al., "Mutagenicity of coolwhite fluorescent light for Salmonella.", *Mutation Research*, vol. 260, No. 1 May 1991, 25-38.

Hartman, Philip S.,"Transillumination can profoundly reduce transformation frequencies.", *Biotechniques*, vol. 11, No. 6 Dec. 1991, 747-748.

Hegner, Martin et al., "Immobilizing DNA on gold via thiol modification for atomic force microscopy imaging in buffer solutions", *FEBS*, vol. 336, No. 3 Dec. 1993, 452-456.

Hegner, Martin et al., "Modified DNA immobilized on bioreactive selfassembled monolayer on gold for dynamic force microscopy imaging in aqueous buffer solution", *J. Vac. Sci. Technol. B*, vol. 14, No. 2, 1996, 1418-1421.

Hegner, Martin et al., "Ultralarge Atomically Flat Template-Stripped Au Surfaces for Scanning Probe Microscopy", *Surface Science*, vol. 291, 1993, 39-46.

Ho, David D. et al., "Characterization of human immunodeficiency virus type 1 variants that encode viral protease with decreased sensitivity to an inhibitor of the viral protease", *Journal of Virology*, vol. 68, No. 3, Mar. 1994, 2016-2020.

Hochuli, E. et al., "Genetic Approach to Facilitate Purification of Recombinant Proteins with a Novel Metal Chelate Adsorbent", *Bio/Technology*, vol. 6, Nov. 1988, 1321-1325.

Hoffman, Les et al., "T4 Endonuclease V Detects UV Transilluminator Damage to Dna in Agarose Gels", *Epicentre Forum*, vol. 3, No. 3, 1996, 1-3.

Holliger, et al., "Diabodies: Small Bivalent and Bispecific Antibody Fragments", *Proceedings of the National Academy of Sciences (PNAS)*, vol. 90, 1993, 6444-6448.

Hollinger, Philipp et al., "Diabodies: small bivalent and bispecific antibody fragments", *PNAS*, Vol. 90, No. 14,1993, 6444-6448.

Houston, John G. et al., "The chemical-biological interface: developments in automated and miniaturised screening technology.", *Current Opinion in Biotechnology*, vol. 8, No. 6, Dec. 1997, 734-740.

Hunter, Tony et al., "The Protein Kinases of Budding Yeast: Six Score and More", *TIBS*, vol. 22, Jan. 1997, 18-22.

Iba, et al., "Comparison of Strategies for the Construction of Libraries of Artificial Antibodies", *Immunology and Cell Biology*, vol. 75, 1997, 217-221.

Jacobson, Stephen C. et al., "Fused quartz substrates for microship electrophoresis", *Analytical Chemistry*, vol. 67, No. 13, Jul. 1, 1995, 2059-2063.

James, F. C., *Journal of Chromatography*, 1991, 569, 389-40.

Jasney, Barbara R., "Insect Viruses Invade Biotechnology", *Science*, vol. 79, 1987-1653.

Kohler, G., et al., "Continuous cultures of fused cells secreting antibody of predefined specificity", *Nature*, vol. 256, Aug. 7, 1975, 495-497.

Korant, Bruce D. et al., "The HIV protease and therapies for aids", *Advances in Experimental Med. and Biol.*, vol. 421, 1997, 279-284.

Kricka, Larry J., "Miniaturization of Analytical Systems", *Clinical Chemistry*, vol. 44, No. 9, 1998, 2008-2014.

Lehrach, H et al., "High throughput tools for gene identification and functional gene analysis", *Nucleic Acid Symp. Ser./Proceedings of the 1988 Miami Bio/Technology Winter Symposium*, vol. 38, 1998, 7-10.

Lemmo, Anthony V. et al., "Characterization of inkjet chemical microdispener for combinatorial library synthesis", *Analytical Chemistry*, vol. 69, No. 4, Feb. 15, 1997, 543-551.

Lijnen, H. R. et al., "Screening Panels of Monoclonal Antibodies using Phage-Displayed Antigen", *Analytical Biochemistry*, vol. 248, No. 2, 1997, 211-215.

Lindahl, T, "The Croonian Lecture, 1996: endogenous damage to DNA." *Philosophical Transactions: Biological Sciences*, vol. 351, No. 1357. Nov. 29, 1996,.

Linford, Matthew R. et al., "Alkyl monolayers on silicon prepared from 1alkenes and hydrogenterminated silicon", *Journal of the American Chemical Society*, vol. 117, 1995, 3145-3155.

Loeb, Daniel D. et al., "Complete Mutegenesis of the Hiv-1 Protease", *Nature*, vol. 340, 1989, 397-400.

Louis, John M. et al., "Autoprocessing of the Hiv-Protease Using Purified Wild-Type and Mutated Fusion Proteins Expressed at High Levels in Eschericia Coli", *Eur. J. Biochem.*, vol. 199, 1991, 361-369.

Lueking, Angelika et al., "Protein Microarrays for Gene Expression and Antibody Screening", *Analytical Biochemistry*, vol. 270, No. 1, 1999, 103-111.

Maggio, Edward T.,"Enzyme-Immunoassay", *Immunoenzyme technique* CRC Press, 1980,186-187.

Maier, Elmar et al., "Automated Array Technologies for Gene Exprerssion Profiling", *Drug Discovery Today*, vol. 2, No. 8 1997, 315-324.

Marks, et al., "By-passing immunication-Human antibodies from V-gene libraries displayed on phage", vol. 222, *J. Mol. Biol.*, 1991, 581-597.

Marshall, Andrew et al., "DNA chips: an array of possibilities", *Nature Biotechnology*, vol. 16, Jan. 998, 27-31.

Jin, X et al., "Sybr Green-1: A New Fluorescent Dye Optimized for Detection of picogram Amounts of DNA in Gels", *Biophysical Journal*, vol. 66, 1994, A159.

John, Joseph F. et al., "Plasmids as Epidemiologic Markers in Nosocomial Gram-Negative Bacilli: Experience at a University and Review of the Literature", *Reviews of Infectious Diseases the University of Chicago*, vol. 8, No. 5, Sep. 1986, 693-704.

Johnston, Stephen A. et al., "Isolation of the yeast regulatory gene GAL4 and analysis of its dosage effects on the galactose/melibiose regulon", vol. 79, *Proceedings of the National Academy of Sciences (PNAS)* Genetics, Nov. 1982, 6971-6975.

Jones, Vivian W. et al., "Microminiaturized Immunoassays Using Atomic Force Microscopy and Compositionally Patterned Antigen Arrays", *Analytical Chemistry* vol. 70, No. 7, Apr. 1, 1998, 1233-1241.

Jones, Peter T. et al., "Replacing the complementarity-determining regions in a human antibody with those from a mouse", *Nature*, vol. 321, 1986, 522-525.

Jonsson, Ulf et al., "Immobilization of Immunoglobulins on Silica Surfaces. Kinetics of Immobilization and Influence of Ionic Strength", *Biochem J.*, vol. 227, No. 2, Apr. 15, 1985, 373-378.

Kane, Ravi S. et al., "Patterning Proteins and Cells Using Soft Lithography", *Biomaterials*, vol. 20, 1999, 2363-2376.

Kaplan, Andrew H. et al., "Selection of multiple human immunodeficiency virus type 1 variants that encode viral proteases with decresed sensitivity to an inhibitor of the viral protease", *Proceedings of the National Academy of Sciences (PNAS)*, vol. 91, Jun. 1994, 5597-5601.

Kemeny, D. M.,"Enyme-Linked Immunoassays", *Immunochemistry 1: A Practical Approach Eds. Johnstone and Turner*, 1997, 147-175.

Kendall, Kevin J. et al., "Plasmid Transfer in Streptomyces lividans: Identification of a kil-kor System Associated with the Transfer Region of pIJ101", *Journal of Bacteriology American Society for Microbiology*, vol. 169, No. 9 Sep. 1987, 4177-4183.

Koh, Howard K. et al., "Sunlight and cutaneous malignant melanoma: evidence for and against causation.", *Photochemistry and Photobiology*, vol. 51, No. 6, 6/90, 765-779.

Martynova, Larisa et al., "Fabricating of plastic microfluid channels by imprinting methods", *Analytical Chemistry*, vol. 69, No. 23, Dec. 1, 1997, 4783- 4789.

Maskos, Uwe et al., "Oligonucleotide hybridizations on glass supports: a novel linker for oligonucleotide synthesis and hybridization properties of oligonucleotides synthesised in situ", *Nucleic Acids Research*, vol. 20, No. 7, 1999, 1679-1684.

Mauracher, Christoph a. et al., "Reduction of rubella Elisa backround using heat denatured sample buffer", *Journal of Immunological Methods*, vol. 145, No. 1-2, Dec. 15, 1991, 251-254.

Mcknight, Steven L., "Functional Relationships between Transcriptional Control Signals of the Thymidine Kinase Gene of Herpes Simplex Virus", *Cell MIT*, vol. 31,Dec. 1982, 355-365.

Merril, Carl R., "Gel-staining techniques", *Methods in Enzymology*, vol. 182, 1990, 477-488.

Mille, Blandine et al., "Two-site immunoassay of recombinant hirudin based on two monoclonal antibodies", vol. 40, No. 5, ISSN: 0009-9147, 1994, 734-739.

Moore, Michael L. et al., "Peptide Substrates and Indibitors of HIV-1 Protease", *Biochemical and Biophysical Research Communications*, vol. 159, No. 2, Dec. 15, 1989, 420-425.

Morrison, et al., "Chimeric human antibody molecules: Mouse antigen- binding domains with human constant region domains", *Proceedings of the National Academy of Sciences (PNAS)*, Vol. 81,1984, 6851-6855.

Mrksich, Milan et al., "Controlling cell attachment on contoured surfaces with self-assembled monolayers of alkanethiolates on gold", *Proceedings of the National Academy of Sciences (PNAS)*, vol. 93, Oct. 1996, 10775-10778.

Nawa, Masaru et al., "Stability of Hemagglutinating Activity of Extracellular and Intracellular Forms of Japanese Encephalitis Virus Exposed to Acidic pH", vol. 40, No. 5, ISSN: 0385-5600,1996, 365-371.

Nikogosyan, D N., "Two-quantum UV photochemistry of nucleic acids: comparison with conventional low-intensity Uv photochemistry and radiation chemistry." *Int. J. Radiat. Biol.*, vol. 57, No. 2, Feb. 1990, 233-299.

Nock, Steffen, "Reversible, site-specific immobilization of polyargininetagged fusio proteins on mica surfaces", *FEBS Letters*, vol. 414, 1997, 233-238.

Noren, Christopher J. et al., "A General Method for Site-Specific Incorporation of Unnatural Amino Acids into Proteins", *Science, American Association for the Advancement of Science*, vol. 244 ,1989,182-188.

Ohyama, et al., "Changes in Glycolipid Expression in Human Testicular Tumor", *Int. J. Cancer*, vol. 45, 1990, 1040-1044.

Okayama and Berg, "A cDNA Cloning Vector That Permits Expression of cDNA Inserts," *Molecular and Cellular Biology*, vol. 3, 1983,280-289.

Pale-Grosdemange, Catherine et al., "Formation of Self-Assembled Monolayers by Chemisorption of Derivatives of Oligo (Ethylene Glycol) of Structure Hs(CH2) 11(OCH2CH2)mOH on Gold", *J. Am. Chem. Soc.*, vol. 113, No. 1, 1991, 12-20.

Pandey, Akhilesh et al., "Proteomics to Study Genes and Genomes", *Nature*, vol. 405, No. 6788, Jun. 15, 2000, 837-846.

PCT/US99/02442, International Search Report mailed Apr. 28, 1999, 7.

PCT/US99/02442, Written Opinion mailed Feb. 16, 2000, 5.

Pease, Ann C. et al., "Light-Generated Oligonucleotide Arrays for Rapid DNA Sequence Analysis", *Proc. Natl. Acad. Sci.*, vol. 91, 1994, 5022-5026.

Pennington, et al., "Proteome analysis: from protein characterization to biological function", *Trends in Cell Biology*, vol. 7, No. 4, 1997, 168-173.

Peraldi, Pascal et al., "Protein-Tyrosine-Phosphatase 2C is Phosphorylated and Inhibited by 44-kDa Mitogen-Activated Protein Kinase", *Proceedings of the National Academy of Sciences (PNAS)*, vol. 91, No. 11 May 1994, 5002-5003.

Pham, Minh-Quan et al., "Human Interleukin-2 Production in Insect (Trichoplusia ni) Larvae: Effects and Partial Control of Proteolysis", *Biotechnology and bioengineering*, vol. 62, No. 2, 1999, 175-182.

Piehler, J. et al., "Multi-analyte determination with a direct optical multi- antibody detection system", *SPIE*, vol. 2504, 1995, 185-194.

Pollet, D. E. et al., "Enzyme-antigen immunoassay for human placental alkaline phosphatase in serum and tissue extracts, and its application as a tumor marker", *Clinical Chemistry*, vol. 31(1) Jan. 1985, 41-45.

Presta, "Antibody Engineering", *Current Opinion in Structural Biology*, vol. 2, 1992, 593-596.

Prime, Kevin L. et al., "Self-Asssembled Organic Monolayers: Model Systems for Studying Absorption of Proteins at Srufaces.", *Science*, vol. 252, 1991, 1164-1167.

Raag, Reetta et al., "Single-Chain Fvs", *The FASEB Journal*, vol. 9, No. 1 Jan. 1995, 73-80.

Rader et al., "Phage Display of Combinatorial Antibody Libraries", *Current Opinion in Biotechnology*, vol. 8, 1997, 503-508.

Ramsay, Graham, "DNA chips: state-of-the art", *Nature Biotechnology*, vol. 16, No. 1, Jan. 1998, 40-44.

Riechmann et al., "Phage Display and Selection of a Site-Directed Randomized Single-Chain Antibody FV Fragment for Its Affinity Improvement", vol. 32, *Biochemistry*, 1993, 8848-8855.

Riechmann et al., "Reshaping human antibodies for therapy", *Nature*, vol. 332, 1988, 323-329.

Roberts, Noel a. et al., "Rational Design of Peptide-Based Hiv Proteinase Inhibitors", *Science*, vol. 248, Apr. 20, 1990, 358-361.

Rowe, Chris a. et al., "Array Biosensor for Simulatneous Identification of Bacterial, Viral and Protein Analytes", *Analytical Chemistry*, vol. 71, No. 17, Sep. 1, 1999, 3846-3852.

Rubin, Gerald M., "Drosophila melanogaster as an Experimental Organism", *Science*, vol. 240, 1988, 1453-1459.

Scarman et al., "Identification of novel species-specific antigens of Mycoplasma hyopneumoniae by preparative SDS-PAGE ELISA profiling", *Microbiology*, vol. 143, 1997, 663-673.

Schneeberger, Christian et al., "Quantitative detection of reverse transcriptase-PCR products by means of a novel and sensitive DNA stain.", *PCR Methods and Applications*, vol. 4, No. 4 Feb. 1995, 234-238.

Schock, Hilary B. et al., "Mutational anatomy of an Hiv-1 protease variant conferring cross-resistance to protease inhibitors in clinical trials", *The Journal of Biological Chemistry*, vol. 271, No. 50, Dec. 13, 1996, 31957-31963.

Scholler, Patrik et al., "Fine-mapping of shotgun template-libraries; an efficient strategy for the systematic sequencing of genomic DNA", *Nucleic Acids Research*, vol. 23, No. 19, Oct. 11, 1995, 3842-3849.

Schuh, Rolf, "Determination of monoclonal antibody specificity byimmunoadsorption and Western blotting", *Journal of Immunological Methods*, vol. 152, 1992, 59-67.

Seurynck-Servoss, Shannon L. et al., "Surface chemistries for antibody microarrays", *Frontiers in Bioscience*, vol. 12, A Journal and Virtual Library May 1, 2007, 3956-3964.

Sharp, Philip A. et al., "Detection of Two Restriction Endonuclease Activities in Haemophilus Parainfluenzae Using Analytical Agarose-Ethidium Bromide Electrophoresis", *Biochemistry*, vol. 12, No. 16 1973, 3055-3063.

Sigal, George B. et al., "A Self-Assembled Monolayer for the Binding and Study of Histidine-tagged Proteins by Surface Plasmon Resonance", *Analytical Chemistry* vol. 68, No. 3, Feb. 1, 1996, 490-497.

Silver, Pamela A. et al., "Amino terminus of the yeast GAL4 gene product is sufficient for nuclear localization", *Proceedings of the National Academy of Sciences (PNAS)*, vol. 81,Oct. 1984, 5951-5955.

Silzel, John W. et al., "Mass-Sensing, Multianalyte Microarray Immunoassay with Imaging Detection", *Clinical Chemistry* vol. 44, No. 9, 1998, 2036-2043.

Singer, Victoria L. et al., "Comparison of Sybr Green I nucleic acid gel stain mutagenicity and ethidium bromide mutagenicity in the Salmonella/mammalian microsome reverse mutation assay (Ames test).", Mutation Research, Vol. 439, No. 1, Feb. 2, 1999, 37-47.

Singer, Victoria L. et al., "Sensitive Fluorescent Stains for Detecting Nucleic Acids in Gels and Solutions.", *Biotechnology* vol. 19, 1994, 68-72.

Singhvi, Rahul et al., "Engineering cell shape and function", *Science*, vol. 264, Apr. 29, 1994, 696-698.

Skalka, Anna M., "Retroviral proteases: first glimpses at the anatomy of a processing machine", *Cell* vol. 56, Mar. 24, 1989, 911-913.

Steinberg, Thomas H. et al., "Sypro orange and Sypro red protein gel stains: one-step fluorescent staining of denaturing gels for detection of nanogram levels of protein.", *Analytical Biochemistry*, vol. 239, No. 2, Aug. 1, 1996, 223-327.

Stennicke, Henning R. et al., "Biochemical characteristics of caspases-3, —6, —7, and —8", *The Journal of Biological Chemistry*, vol. 272, No. 41, Oct. 10, 1997, 25719-25723.

Stern, David F. et al., "Spk1, a new kinase from Saccharomyces cerevisiae, phosphorylates proteins on serine, threonine, and tyrosine", *Molecular and Cellular Biology*, vol. 11, No. 2, Feb. 1991, 987-1001.

Stevenson, A. J. et al., "Antibodies to collagen IV in the serum of workers exposed to hydrocarbons and Volatile organic chemicals", *Biomarkers*, vol. 2 1997, 63-65.

Sundberg, Steven A. et al., "Spatially-Addressable Immobilization of Macromolecules on Solid Supports", *J. Am. Chem. Soc.*, vol. 117, No. 49, 1995, 12050-12057.

Talanian, Robert V. et al., "Substrate Specificities of Caspases Family Proteases",*The Journal of Biological Chemistry*, vol. 272, No. 15, Apr. 11, 1997, 9677-9682.

Teixeira-Gomes et al., "Identification and characterization of *Brucella ovis* immunogenic proteins using two-dimensional electrophoresis and immunoblotting", *Electrophoresis*, vol. 18 1997, 1491-1497.
Thornberry et al., "Interleukin-1beta Converting Enzyme", *Methods in Enzymology*, vol. 244, 1994, 615-631.
Tuma, Rabiya S. et al., "Characterization of SYBR Gold nucleic acid gel stain: a dye optimized for use with 300-nm ultraviolet transilluminators.", *Analytical Biochemistry*, vol. 268, No. 2, Mar. 15, 1999, 278-288.
Ulmanen, I et al., "Transcription and Translation of Foreign Genes in Bacillus subtilis by the Aid of a Secretion Vector", *Journal of Bacteriology*, vol. 162, No. 1, Apr. 1985, 176-182.
Unla et al., *Electrophoresis*; vol. 18, 1997, 2071-2077.
Unlu, Mustafa et al., "Difference gel electrophoresis: a single gel method for detecting changes in protein extracts.", *Electrophoresis*, vol. 18, No. 11, Oct. 1997, 2071-2077.
Venien, Annie et al., "Production and Epitopic Characterization of Monoclonal Antibodies Against Bovine p-Lactoglobulin", ISSN: 0022-0302 1997, vol. 80, No. 9, 1977-1987.
Villa, Pascal et al., "Caspases and caspase inhibitors", *TIBS*, vol. 22, Oct. 1997, 388-393.
Wagner, Peter et al., "Bioreactive Self-Assembled Monolayers on Hydrogen-Passivated Si(111) as a New Class of Atomically Flat Substrates for Biological Scanning Probe Microscopy", *Journal of Structural Biology*, vol. 119, 1997, 189-201.
Wagner, Peter et al., "Covalent immobilization of native biomolecules onto Au(111) via N-hydroxysuccinimide ester funtionalized self-assembled monolayers for scanning probe microscopy", *Biophysical Journal*, vol. 70, May 1996, 2052-2066.
Wagner, Peter et al., "Formation and in Situ Modification of Monolayers Chemisorbed on Ultraflat Template-Stripped Gold Surfaces", *Langmuir*, vol. 11, No. 10, 1995, 3867-3875.
Wagner, Peter et al., "Omega-functionalized self-assembled monolayers chemisorbed on ultraflat Au(111) surfaces for biological scanning probe microscopy in aqueous buffers", *J. Vac. Sci. Technol. B*, vol. 14, No. 2, 1996, 1466-1471.
Wallace, Lesley A. et al., "Molecular Characterization of Envelope Antigenic Variants of Hepatitis B Virus from Spain", vol. 170, No. 5, ISSN: 0022-1899 1994, 1300-1303.
Ward, Judith M. et al., "Construction and characterisation of a series of multicopy promoter-probe plasmid vectors for Streptomyces using the aminoglycoside phosphotransferase gene from Tn5 as indicator", Mol. Gen. *Genet.*, vol. 203, 1986, 468-478.
Weiner, Michael P. et al., "Site-Directed Mutagenesis of Double-Stranded DNA by the Polymerase Chain Reaction", *Gene*, vol. 151, 1994, 119-123.
White, H W. et al., "GelStar Nucleic Acid Gel Stain: High Sensitivity Detection in Gels", *Biotechniques*, vol. 26, No. 5, May 1999, 984-988.
Wilson, Curtis M., "Staining of proteins on gels: comparisons of dyes and procedures.", *Methods in Enzymology*, vol. 91, 1983, 236-247.
Wilson, Keith P. et al., "Structure and mechanism of interleukin-1 beta, converting enzyme", *Nature*, vol. 370, Jul. 28, 1994, 270-275.
Wondrak, Ewald M. et al., "Influence of flanking sequences on the dimer stability of human immunodeficiency virus type 1 protease", *Biochemistry*, vol. 35, No. 39, 1996, 12957-12962.
Woo, Savio L. et al., "A Sensitive and Rapid Method for Recombinant Phage Screening", *Methods in Enzymology*, vol. 68 1979, 389-395.
Wu, Jin et al., "Structural Basis for a Specificity of Retroviral Proteases", *Biochemistry*, vol. 37, No. 13, 1998, 4518-4526.
Xie, Kewei et al., "Nuclear dot antigen may specify transcriptional domains in the nucleus", *Molecular and Cellular Biology*, vol. 13, No. 10, Oct. 1993, 6170-6179.
Xie, Kewei et al., "Two short autoepitopes on the nuclear dot antigen are similar to epitopes encoded by the Epstein-Barr virus", *Proceedings of the National Academy of Sciences* (*PNAS*), vol. 92, No. 5, Feb. 1995, 1639-1643.
Yang, Te-Tuan et al., "Dual color microscopic imagery of cells expressing the green fluorescent protein and a red-shifted variant.", *Gene*, vol. 173, 1996, 19-23.
Yang, Charles H. et al., "Higher order structure is present in the yeast nucleus: autoantibody probes demonstrate that the nucleolus lies opposite the spindle pole body", *Chromosoma*, vol. 98, No. 2, Aug. 1989, 123-128.
Yang, Te-Tuan et al., "Improved fluorescence and dual color detection with enhanced blue and green variants of the green fluorescent protein.", *The Journal of Biological Chemistry*, vol. 273, No. 14, Apr. 3, 1998, 8212-8216.
Zapata, Gerardo et al., "Engineering Linear F(ab') .sub. 2 Fragments for Efficient Production in Escherichia coli and Enhanced Antiproliferative Activity", vol. 8, No. 10, *Protein Engineering*, 1995, 1057-1062.
Zhang, Guohong et al., "An enhanced green fluorescent protein allows sensitive detection of gene transfer in mammalian cells", *Biochemical and Biophysical Research Communications*, vol. 227, No. 3, Oct. 23, 1996, 707-711.
Zhu, Zhengrong et al., "Directly labeled DNA probes using fluorescent nucleotides with different length linkers",*Nucleic Acids Research*, vol. 22, No. 16, Aug. 25, 1994, 3418-3422.
Ziegler, A. et al., "Short Communication; Cucumber Mosaic Cucumovirus Antibodies from a Synthetic Phage Display Library", *Virology*, vol. 214, No. 1, Dec. 1995, 235-238.
Zona, Steven J. et al., "PBXL Fluorescent Dyes for Ultrasensitive Direct Detection", *Journal of Fluorescence*, vol. 9, No. 3, 1999, 197-208.

* cited by examiner

MICROARRAYS AND USES THEREFOR

This application is a continuation and claims the right of priority under 35 U.S.C. §120 to U.S. Ser. No. 10/035,368, filed Oct. 26, 2001, now abandoned, which is a divisional application of U.S. Ser. No. 09/245,615, filed Feb. 4, 1999 now U.S. Pat. No. 7,794,946, which claims the benefit of priority under 35 U.S.C. §119 of U.S. Ser. No. 60/073,605, filed Feb. 4, 1998 (now abandoned), the entire contents of each of which is incorporated herein by reference.

FIELD OF THE INVENTION

The invention disclosed herein relates to new methods of using microarray technologies. The methods are useful for identifying and characterizing specific antibodies as well as the characterization of different tissues or cells by protein or nucleic acid analysis.

BACKGROUND OF THE INVENTION

Recent breakthroughs in nucleic acid sequencing technology have made possible the sequencing of entire genomes from a variety of organisms, including humans. The potential benefits of a complete genome sequence are many, ranging from applications in medicine to a greater understanding of evolutionary processes. These benefits cannot be fully realized, however, without an understanding of how and where these newly sequenced genes function.

Traditionally, functional understanding started with recognizing an activity, isolating a protein associated with that activity, then isolating the gene, or genes, encoding that protein. The isolated protein was also used to generate antibody reagents. Specific antibodies and fragments of the isolated gene were both employed to study tissue expression and function.

Several methods have been used to study protein expression patterns including in situ hybridization studies of tissue sections and northern blots. These methods are both time consuming and require relatively large amounts of material to perform successfully.

Antibodies that bind to specific antigens have been produced by a variety of methods including immunization of animals, fusion of mammalian spleen cells to immortalized cells to produce hybridomas, random peptide generation using phage or bacterial display and constrained peptide libraries. Regardless of how the desired antibody is generated, the methods currently available to identify one with a particular binding specificity are generally laborious and incapable of the simultaneous testing of large numbers of unknowns.

One method involves binding the antigen to a porous membrane, such as nitrocellulose, contacting the membrane with a source of test antibodies, then determining whether or not any of the test antibodies has bound to the antigen. This method only allows the testing of one source of test antibodies per piece of porous membrane, making the method both inconvenient and wasteful of materials.

Antibody/antigen reactions can also be evaluated in plastic plates, such as 96-well microtiter plates, using methods similar to those described above. This method is likewise limited in the number of samples that can be tested in any one assay, thus requiring many assays to fully evaluate a large number of antibody unknowns. Chang (U.S. Pat. No. 4,591,570, issued May 27, 1986) describes an array of a limited number of characterized antibodies to known antigens on a glass surface that can be used to bind to specific antigens on the surface of whole cells.

Recently new technologies have arisen that allow the creation of microarrays containing thousands or millions of different elements. Such array technology has been applied mainly to forming arrays of individual nucleic acids (see, for example, Marshall and Hodgson, Nature Biotech. 16:27-31, 1998; Ramsay, Nature Biotech. 16:40-44, 1998), in particular short oligonucleotides synthesized in situ.

Methods are needed to simply and rapidly screen very large numbers of uncharacterized antibodies for those specific for a given antigen as well as for the characterization of tissues and cells by nucleic acid and/or protein analysis. The invention described herein addresses that need.

BRIEF DESCRIPTION OF THE INVENTION

The invention disclosed herein comprises methods of using microarrays to simplify analysis and characterization of genes and their function. In one aspect of the invention the methods are used to identify and characterize antibodies having binding affinity for a specific target antigen. This method comprises contacting an array of uncharacterized antibodies bound to a solid surface with at least one target antigen and identifying the antibodies to which the target antigen binds. The method can be performed under a variety of conditions to identify antibodies with a range of binding affinities.

A second aspect of the invention comprises a method of determining gene expression at the protein level comprising contacting an array of characterized or uncharacterized antibodies on a solid surface with one or more proteins and identifying the antibodies to which said protein(s) binds. This method can be further used to compare the protein expression in two different populations of cells, such as normal cells and cancer cells or resting cells and stimulated cells. A related embodiment can be used as a tool in the diagnosis of various disorders.

A further aspect of the invention comprises a method of determining gene expression at the protein level comprising contacting a microarray of nucleic acid samples derived from a variety of different sources with one or more nucleic acid probes then identifying the sample or samples to which the probe binds.

DETAILED DESCRIPTION OF THE INVENTION

Figure 1A:
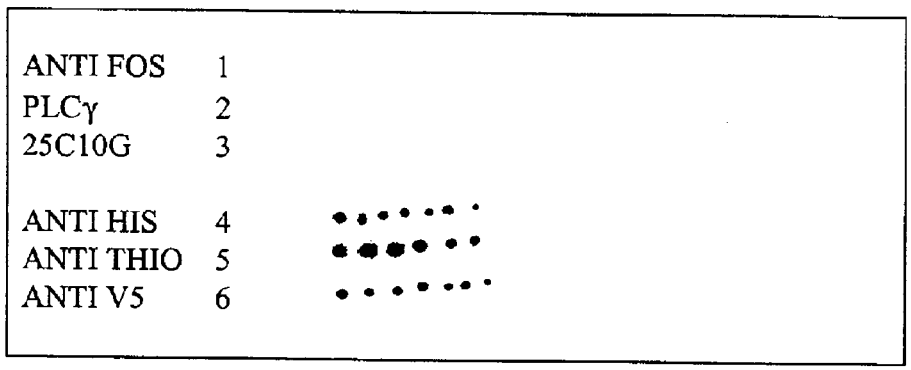
FIGS. 1A, 1B, and 1C show microarrays of antibodies bound to positively charged nylon, reacted with antigen and detected by non-fluorescent means.

The present invention discloses methods of using microarrays to simplify analysis and characterization of genes and their function. In a first aspect of the invention the methods are used for identifying and characterizing antibodies having binding specificity to a particular antigen or set of antigens. This method utilizes microarray technology to create ordered matrices of large numbers of uncharacterized antibodies which can then be contacted with antigen under a variety of conditions. The method is rapid and simple to perform and is applicable to the simultaneous screening of very large numbers of antibodies.

Briefly, uncharacterized antibodies are bound to a solid surface in an array format consisting of discrete spots whose spatial location can be easily identified. Each location represents an antibody from a known source, such as a particular hybridoma growing in a well in a 96-well microtiter plate. The space between the antibody spots is treated to minimize non-specific binding to the solid support. The arrayed antibodies are then contacted with an antigen, or a set of antigens, for which specific antibodies are sought. The antigen solution is left in contact with the array for an amount of time sufficient to allow antigen:antibody complexes to form (generally 10 minutes to 2 hours), then the unbound antigen is washed away under suitable conditions. Bound antigen is detected at a particular antibody spot using one of a variety of detection methods, thus identifying the source of an antibody specific for the particular antigen.

The term "antibody" is used herein in the broadest sense and specifically includes intact monoclonal antibodies, polyclonal antibodies, multispecific antibodies (e.g. bispecific antibodies) formed from at least two intact antibodies, and antibody fragments, including single chain antibodies, so long as they exhibit the desired binding properties as described herein.

Various procedures well-known in the art may be used for the production of polyclonal antibodies to an epitope or antigen of interest. A host animal of any of a number of species, such as rabbits, goats, sheep, horse, cow, mice, rats, etc. is immunized by injection with an antigenic preparation which may be derived from cells or microorganisms, or may be recombinantly or synthetically produced. Various adjuvants well known in the art may be used to enhance the production of antibodies by the immunized host, for example, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, liposomes, potentially useful human adjuvants such as BCG (Bacille Calmette-Guerin) and *Propionibacterium acanes*, and the like.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Preferred antibodies are mAbs, which may be of any immunoglobulin class including IgG, IgM, IgE, IgA, and any subclass or isotype thereof.

In addition to their specificity, monoclonal antibodies are advantageous in that they are synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567, incorporated by reference herein). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies contemplated for use herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, *Curr. Op. Struct. Biol.*, 2:593-596 (1992). The humanized antibody includes a PRIMATIZED™ antibody wherein the antigen-binding region of the antibody is derived from an antibody produced by immunizing macaque monkeys with the antigen of interest.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al. *Protein Eng.* 8(10):1057-1062 (1995)); single-chain antibody molecules; and multispecific antibodies formed from antibody fragments.

Particularly preferred in the practice of the invention are single-chain antibodies. "Single-chain" or "sFv" antibodies are antibody fragments comprising the $V_H$ and $V_L$ domains of an antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFvs see Pluckthun in *The Pharmacology of Monoclonal Antibodies*, vol. 113, Rosenburg and Moore eds., Springer-Verlag, New York, pp. 269-315 (1994).

Large quantities of single chain antibodies with uncharacterized randomized binding specificity can be produced using a number of methodologies known in the art. Recombinant antibody libraries can be created in filamentous phage particles (Daniels and Lane, Methods 9(3):494-507, 1996; Reichmann and Weill, Biochemistry 32(34):8848-8855; Rader and Barbas, Curr Opin Biotechnol 9(4):503-508, 1997; Iba and Kurosawa, Immunol Cell Biol 75(2):217-221, 1997, WO 90/05144, WO 92/01047, WO 92/20791, WO 93/19172, GB 9722131.8, GB9810228.8 and GB 9810223.9, all of which are incorporated by reference herein in their entirety), for example, or similarly in yeast, bacteria, and the like. Other methods for creating random libraries of sFvs include various solid state synthesis methods.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The antibodies employed in the invention can be isolated prior to creating a microarray. An "isolated" molecule, whether an antibody, antigen or nucleic acid, is one which has been identified and separated and/or recovered from a component of its natural environment. Contaminant components of its natural environment are materials which would interfere with particular uses for the molecule, and may include enzymes, hormones, and other proteinaceous or nonproteinaceous solutes. In preferred embodiments, a protein will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated protein includes the protein in situ within recombinant cells since at least one component of the protein's natural environment will not be present. Ordinarily, however, isolated protein will be prepared by at least one purification step. Unpurified antibodies, such as those found in serum, can also be employed in the present invention.

By "isolated" in reference to nucleic acid is meant a polymer of 14, 17, 21 or more contiguous nucleotides, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular (i.e., chromosomal) environment. Thus, the sequence may be in a cell-free solution or placed in a different cellular environment. The term does not imply that the sequence is the only nucleotide sequence present, but that it is essentially free (about 90-95% pure at least) of non-nucleotide material naturally associated with it and thus is meant to be distinguished from isolated chromosomes.

One particularly useful method of isolating antibodies, such as single chain antibodies from a cell extract, is affinity purification. Resins suitable for antibody purification are well known in the art, for example, protein A SEPHAROSE™. A recombinant antibody can be engineered to contain an affinity purification tag to facilitate its purification. Resins suitable for antibody purification are well known in the art, for example, protein A SEPHAROSE™ resin.

Affinity purification tags are generally peptide sequences that can interact with a binding partner immobilized on a solid support. Synthetic DNA sequences encoding multiple consecutive single amino acids, such as histidine, when fused to the expressed protein, may be used for one-step purification of the recombinant protein by high affinity binding to a resin column, such as nickel SEPHAROSE™ resin. An endopeptidase recognition sequence can be engineered between the polyamino acid tag and the protein of interest to allow subsequent removal of the leader peptide by digestion with enterokinase, and other proteases. Sequences encoding peptides such as the chitin binding domain (which binds to chitin), biotin (which binds to avidin and strepavidin), and the like can also be used for facilitating purification of the protein of interest. The affinity purification tag can be separated from the protein of interest by methods well known in the art, including the use of inteins (protein self-splicing elements, Chong, et al, Gene 192:271-281, 1997).

By using an amount of resin with binding sites sufficient for only a small portion of the antibody present in the unpurified mixture, the process of isolation can be used to simultaneously normalize yield and isolate the antibody. For example, although each sample will contain a different and unknown amount of antibody protein, the samples can be contacted with an amount of resin whose maximum binding capacity is 10 mgs. Thus any antibody greater than this amount will pass through the resin unbound. The maximum bound amount can then be eluted from the resin.

Methods for creating microarrays are known in the art including printing on a solid surface using pins (passive pins, quill pins, and the like) or spotting with individual drops of solution. Passive pins draw up enough sample to dispense a single spot. Quill pins draw up enough liquid to dispense multiple spots. Bubble printers use a loop to capture a small volume which is dispensed by pushing a rod through the loop. Microdispensing uses a syringe mechanism to deliver multiple spots of a fixed volume. In addition, solid supports, can be arrayed using piezoelectric (ink jet) technology, which actively transfers samples to a solid support.

One method is described in Shalon and Brown (WO 95/35505, published Dec. 28, 1995) which is incorporated herein by reference in its entirety. The method and apparatus described in Shalon and Brown can create an array of up to six hundred spots per square centimeter on a glass slide using a volume of 0.01 to 100 nl per spot. Suitable concentrations of antibody range from about 1 ng/µl to about 1 µg/µl. In the present invention, each spot can contain one or more than one distinct antibody.

Other methods of creating arrays are known in the art, including photolithographic printing (Pease, et al, *Proc. Natl. Acad. Sci. USA*, 91(11):5022-5026, 1994) and in situ synthesis. While known in situ synthesis methods are less useful for synthesizing polypeptides long enough to be antibodies, they can be used to make polypeptides up to 50 amino acids in length, which can serve as binding proteins as described below.

The microarrays can be created on a variety of solid surfaces such as plastics (e.g. polycarbonate), complex carbohydrates (e.g. agarose and SEPHAROSE™), acrylic resins (e.g. polyacrylamide and latex beads), and nitrocellulose. Preferred solid support materials include glass slides, silicon wafers, and positively charged nylon. Specific examples of suitable solid supports are described in the Examples below.

Methods for covalent attachment of antibodies to a solid support are known in the art. Examples of such methods are found in Bhatia, et al, Anal. Biochem. 178(2):408-413, 1989; Ahluwalia, et al, Biosens. Bioelectron. 7(3):207-214, 1992; Jonsson, et al, Biochem. J. 227(2):373-378, 1985; and Freij-Larsson, et al, Biomaterials 17(22):2199-2207, 1996, all of which are incorporated by reference herein in their entirety. Proteins may additionally be attached to a solid support using methods described in the examples below.

Methods of reducing non-specific binding to a solid surface are well known in the art and include washing the arrayed solid surface with bovine serum albumin (BSA), reconstituted non-fat milk, salmon sperm DNA, porcine heparin, and the like (see Ausubel, et al., Short Protocols in Molecular Biology, 3rd ed. 1995).

The arrays used to identify antigen-specific antibodies are contacted with a solution containing one or more known antigens in order to identify antibodies in the array with binding specificity for the antigen. The antigens are often proteins, although they may also be organic chemical compounds, carbohydrates, nucleic acids, and the like. They may be isolated or semi-isolated, recombinant or naturally occurring. The amount of antigen used can vary from about 1-100 ng/µl. The antigen is left in contact with the array for an amount of time sufficient for antibody:antigen complexes to form, should one of the antibodies in the array be specific for the antigen. The amount of time sufficient for this purpose will range from 5 minutes to 24 hours, and will generally be from 0.5 to 2 hours.

One antigen of particular interest in the practice of the invention is recombinant protein, either a full-length gene product or a fragment thereof, for example an Expressed Sequence Tag (or EST fragment). EST fragments are relatively short cDNA sequences that have been randomly generated and sequenced, generally as part of an ongoing effort to map an entire genome (Adams, et al, Science 252(5013): 1651-1656, 1991). Large numbers of these sequences are available in public databases. The identity of the proteins encoded by the vast majority of these sequences is unknown. The following discussion, although directed to the expression of EST-encoded peptides, is equally applicable to any expressed product of a nucleic acid sequence, including full-length proteins.

Techniques are available in the art by which cells can be genetically engineered to express the peptide encoded by a given EST fragment. The methods of the invention can then be used to identify antibodies specific for the peptide. These antibodies are then useful as reagents that can be employed in purification and identification of the full-length protein, and in other experimental procedures designed to elucidate the protein's location and function.

Prokaryotic hosts are, generally, very efficient and convenient for the production of recombinant proteins and are, therefore, one type of preferred expression system for EST fragments. Prokaryotes most frequently are represented by various strains of E. coli. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119, and the like; suitable phage or bacteriophage vectors may include λgt10, λgt11, and the like; and suitable virus vectors may include pMAM-neo, PKRC and the like. Preferably, the selected vector of the present invention has the capacity to replicate in the selected host cell.

Recognized prokaryotic hosts include bacteria such as E. coli and those from genera such as Bacillus, Streptomyces, Pseudomonas, Salmonella, Serratia, and the like. However, under such conditions, the polypeptide will not be glycosylated. The prokaryotic host selected for use herein must be compatible with the replicon and control sequences in the expression plasmid.

To express an EST fragment in a prokaryotic cell, it is necessary to operably link the gene sequence to a functional prokaryotic promoter such as the T7 promoter or RSC promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, reca, lacZ, LacI, and gal promoters of E. coli, the α-amylase (Ulmanen et al., J. Bacteriol. 162:176-182, 1985) and the sigma-28-specific promoters of B. subtilis (Gilman et al., Gene sequence 32:11-20(1984)), the promoters of the bacteriophages of Bacillus (Gryczan, In: The Molecular Biology of the Bacilli, Academic Press, Inc., NY (1982)), Streptomyces promoters (Ward et at., Mol. Gen. Genet. 203:468-478, 1986), and the like. Exemplary prokaryotic promoters are reviewed by Glick (J. Ind. Microbiol. 1:277-282, 1987); Cenatiempo (Biochimie 68:505-516, 1986); and Gottesman (Ann. Rev. Genet. 18:415-442, 1984).

Proper expression in a prokaryotic cell also requires the presence of a ribosome binding site upstream of the gene sequence-encoding sequence. Such ribosome binding sites are disclosed, for example, by Gold et at. (Ann. Rev. Microbiol. 35:365-404, 1981). The selection of control sequences, expression vectors, transformation methods, and the like, are dependent on the type of host cell used to express the gene.

Host cells which may be used in the expression systems of the present invention are not strictly limited, provided that they are suitable for use in the expression of the peptide of interest. Suitable hosts may often include eukaryotic cells. Preferred eukaryotic hosts include, for example, yeast, fungi, insect cells, and mammalian cells either in vivo, or in tissue culture. Mammalian cells which may be useful as hosts include HeLa cells, cells of fibroblast origin such as VERO, 3T3 or CHOK1, HEK 293 cells or cells of lymphoid origin (such as 32D cells) and their derivatives. Preferred mammalian host cells include SP2/0 and JS58L, as well as neuroblastoma cell lines such as IMR 332 and PC12 which may provide better capacities for correct post-translational processing.

In addition, plant cells are also available as hosts, and control sequences compatible with plant cells are available, such as the cauliflower mosaic virus 35S and 19S, nopaline synthase promoter and polyadenylation signal sequences, and the like. Another preferred host is an insect cell, for example the Drosophila larvae. Using insect cells as hosts, the Drosophila alcohol dehydrogenase promoter can be used. Rubin, Science 240:1453-1459, 1988). Alternatively, baculovirus vectors can be engineered to express large amounts of peptide encoded by an EST fragment in insects cells (Jasny, Science 238:1653, 1987); Miller et al., In: Genetic Engineering (1986), Setlow, J. K., et al., eds., Plenum, Vol. 8, pp. 277-297).

Any of a series of yeast gene sequence expression systems can be utilized which incorporate promoter and termination elements from the actively expressed gene sequences coding for glycolytic enzymes which are produced in large quantities when yeast are grown in media rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). For a mammalian host, several possible vector systems are available for the expression of and EST fragment.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of an EST fragment in eukaryotic hosts involves the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast ga14 gene sequence promoter (Johnston et al., Proc. Natl. Acad. Sci. (USA) 79:6971-6975, 1982); Silver et al., Proc. Natl. Acad. Sci. (USA) 81:5951-5955, 1984), the CMV promoter, the EF-1 promoter, and the like.

An EST fragment and an operably linked promoter may be introduced into a recipient prokaryotic or eukaryotic cell either as a nonreplicating DNA (or RNA) molecule, which may either be a linear molecule or, more preferably, a closed covalent circular molecule (a plasmid). Since such molecules are incapable of autonomous replication, the expression of the gene may occur through the transient expression of the introduced sequence. Alternatively, permanent or stable expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by cotransfection. Common selectable marker gene sequences include those for resistance to antibiotics such as ampicillin, tetracycline, kanamycin, bleomycin, streptomycin, hygromycin, neomycin, Zeocin™, and the like. Selectable auxotrophic gene sequences include, for example, hisD, which allows growth in histidine free media in the presence of histidinol.

Additional elements may also be needed for optimal synthesis of single chain binding protein mRNA. These elements may include splice signals, as well as transcription promoters, enhancers, and termination signals. cDNA expression vectors incorporating such elements include those described by Okayama, Mol. Cell. Bio. 3:280, 1983.

The recombinant antigen may be produced as a fusion protein. When two protein-coding sequences not normally associated with each other in nature are in the same reading frame the resulting expressed protein is called a "fusion protein" as two distinct proteins have been "fused" together. Fusion proteins have a wide variety of uses. For example, two functional enzymes can be fused to produce a single protein with multiple enzymatic activities or short peptide sequences, such as epitope tags or affinity purification tags (see above), can be fused to a larger protein and serve as aids in purification or as means of identifying the expressed protein by serving as epitopes detectable by specific antibodies.

Epitope tags are short peptide sequences that are recognized by epitope-specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemagglutinin (HA), the peptide Phe-His-His-Thr-Thr, chitin binding domain, and the like.

A fusion protein may be a means by which the recombinant antigen protein can be easily detected. For example, the fusion component can itself be a detectable moiety, such as fluorescent protein (fluorescent green protein, fluorescent yellow protein, and the like), or alternatively can be one member of a specific binding pair (such as biotin and streptavidin, for example) which can be detected by reacting with the other member conjugated to a detectable substance.

The foregoing elements can be combined to produce vectors suitable for use in the methods of the invention. Those of skill in the art would be able to select and combine the elements suitable for use in their particular system.

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Suitable prokaryotic vectors include plasmids such as those capable of replication in *E. coli* (for example, pBR322, ColE1, pSC101, PACYC 184, itVX, pRSET, pBAD (Invitrogen, Carlsbad, Calif.), and the like). Such plasmids are disclosed by Sambrook (cf. "Molecular Cloning: A Laboratory Manual", second edition, edited by Sambrook, Fritsch, & Maniatis, Cold Spring Harbor Laboratory, (1989)). *Bacillus* plasmids include pC194, pC221, pT127, and the like, and are disclosed by Gryczan (In: The Molecular Biology of the Bacilli, Academic Press, NY (1982), pp. 307-329). Suitable *Streptomyces* plasmids include p1J101 (Kendall et al., J.

Bacteriol. 169:4177-4183, 1987), and *Streptomyces* bacteriophages such as φC31 (Chater et al., In: Sixth International Symposium on Actinomycetales Biology, Akademiai Kaido, Budapest, Hungary (1986), pp. 45-54). *Pseudomonas* plasmids are reviewed by John et al. (Rev. Infect. Dis. 8:693-704, 1986), and Izaki (Jpn. J. Bacteriol. 33:729-742, 1978).

Suitable eukaryotic plasmids include, for example, BPV, vaccinia, SV40, 2-micron circle, pCDN3.1 (Invitrogen), and the like, or their derivatives. Such plasmids are well known in the art (Botstein et al., Miami Wntr. Symp. 19:265-274, 1982); Broach, In: "The Molecular Biology of the Yeast *Saccharomyces*: Life Cycle and Inheritance", Cold Spring Harbor Laboratory, Cold Spring Harbor, N.Y., p. 445-470 (1981); Broach, Cell 28:203-204, 1982); Dilon et at., J. Clin. Hematol. Oncol. 10:39-48, 1980); Maniatis, In: Cell Biology: A Comprehensive Treatise, Vol. 3, Gene Sequence Expression, Academic Press, NY, pp. 563-608 (1980).

Once antibody:antigen complexes have been formed and unbound antigen washed away under suitable conditions, the antibody:antigen complexes can be detected using one of several techniques known in the art. Suitable washing conditions are known to those skilled in the art (see, for example, Ausubel, et al, Short Protocols in Molecular Biology, 3rd ed. 1995). Exemplary washing conditions are shown in the examples below.

For detection in the case of recombinant antigens, expression vectors can be used that form chimeric fusion peptides as described above. The epitope tagged antigen can be detected using an antibody specific for the tag sequence. This antibody may be itself detectably labeled or can be detected with a third detectably-labeled antibody. Alternatively, the antigen can be complexed with biotin and detected using detectably-labeled avidin or streptavidin. The antigen itself can also be detectably labeled, such as with a fluorescent dye compound.

The term "detectably labeled" as used herein is intended to encompass antigen directly coupled to a detectable substance, such as a fluorescent dye, and antigen coupled to a member of binding pair, such as biotin/streptavidin, or an epitope tag that can specifically interact with a molecule that can be detected, such as by producing a colored substrate or fluorescence.

Substances suitable for detectably labeling proteins include fluorescent dyes such as fluorescein isothiocyanate (FITC), fluorescein, rhodamine, tetramethyl-rhodamine-5-(and 6)-isothiocyanate (TRITC), Texas red, cyanine dyes (Cy3 and Cy5, for example), and the like; and enzymes that react with calorimetric substrates such as horseradish peroxidase. The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

The formation of antibody:antigen complexes can be performed under a variety of conditions to identify antibodies with varying binding characteristics. Antigen-containing reaction solutions can contain varying degrees of salt or be conducted at varying pH levels. In addition, the binding reaction can be carried out at varying temperatures. Each set of conditions will identify antibodies with different affinity for the antigen. For example, antibodies that bind at pH 2 may have utility under highly acidic conditions such as those that exist in the stomach. Similarly, antibodies that bind at temperatures near boiling may be useful in studying thermophilic organisms. In general pH conditions will range from 2-10 (most preferably around pH 8), temperatures from 0° C.-100° C. and salt conditions from 1 μM to 5 M (in the case of NaCl).

Affinity constants are a measure of the interaction between a particular ligand and its cognate receptor. The "binding affinity" or the measure of the strength of association between a particular antibody:antigen interaction is generally measured by affinity constants for the equilibrium concentrations of associated and dissociated configurations of the antibody and its antigen. Preferably the binding of the antigen should occur at an affinity of about $k_a = 10^{-6}$ M or greater to be useful for the present invention, with greater than about $10^{-7}$ M being more preferable, and most preferably between about $10^{-8}$ M and about $10^{-11}$ M. Antibody fragments will generally have affinities in the range of about $10^{-6}$ M to $10^{-7}$ M.

In another embodiment of the invention, microarrays of uncharacterized antibodies are used to compare the protein expression profiles of cells. For example, comparisons can be made between a population of cells from one tissue, such as arterial endothelial cells, and a second tissue, such as venous endothelial cells or from cells derived from a particular tissue but from different species. Comparisons can be made between normal cells and cells from the same tissue type that originate from an individual with a pathogenic disorder. For example, comparisons can be made between normal cells and cancer cells. Comparisons can additionally be made between cells in a resting state and cells in an activated state, for example, resting T-cells and activated T-cells.

In another example, the disclosed arrays are useful for evaluating the expression of proteins by pathogens, such as, for example, bacteria, parasites, viruses, and the like. A solution (such as a lysate) made from the pathogen which represents all proteins expressed by the pathogen can be used to contact an antibody array to identify antibodies recognizing pathogen-expressed proteins. These antibodies have utility as diagnostic agents as well as potential therapeutics.

Cellular lysates can be used as "antigens" as described above and reacted with two identical microarrays. Antibodies reactive in one array but not the other would indicate the presence of a differentially expressed protein. This antibody is then useful for the subsequent isolation and identification of those proteins that are different in two populations of cells. In the case of normal and cancer cells, for example, one may be able to identify proteins expressed in the cancer cell that contribute to its malignant state.

In a further aspect of the invention, microarrays can be composed of previously characterized antibodies. These microarrays have a variety of uses, one of which is cell profiling. For example, an array can be composed of antibodies that recognize a set of antigens known to be present in activated T-cells but not in resting T-cells. A population of T-cells can then be lysed and the lysate contacted with the array to determine if the population has the profile of activated or resting T-cells.

Microarrays and the methods disclosed herein can be used in methods of diagnosing particular disorders. For example, a collection of antibodies specific for a range of antigens associated with one or more disorders can be arrayed and contacted with a bodily fluid containing antigens whose presence, or absence, would indicate a particular disorder. The advantage of using a microarray over a conventional immunoassay is the ability to include a population of antibodies diagnostic for a variety of disorders on a single surface, significantly reducing time, costs and materials needed to effect a diagnosis.

For example, if a patient presents with symptoms that are characteristic of several distinct disorders which can be distinguished on the basis of the presence or absence of one or more proteins, a single microarray assay could be used to make a specific diagnosis, thus allowing the patient to be properly treated. Patients suffering from stroke or brain infarcts release several proteins into cerebrospinal fluid, examples of which are neuron specific enolyse (NSE) from neuronal cells and S-100 from glial cells and astrocytes. Such proteins are not released in conditions that may have similar symptoms, such as drug reactions, making proper diagnosis more difficult. A diagnostic array could readily detect these and other proteins in the CSF, leading to a rapid clinical diagnosis and treatment.

In another aspect of the invention microarrays are employed to characterize protein expression patterns using nucleic acid samples. Briefly, nucleic acid molecules from a whole cell or tissue are applied to a solid support using a microarray format. The arrayed nucleic acid samples are then contacted with a nucleic acid probe specific for a gene encoding a known protein. The probe solution is left in contact with the array for an amount of time sufficient to allow sample: probe complexes to form, then the unbound probe is washed away under suitable conditions (see, for example, Ausubel, et al, Short Protocols in Molecular Biology, 3rd ed. 1995 and the examples below). Bound probe is detected at one or more nucleic acid sample spots using one of a variety of detection methods.

This aspect of the invention has a variety of uses. For example, the microarray can be constructed from nucleic acid samples isolated from a single tissue type but from a large number of species, with each spot representing a particular species. Thus in a single assay format one can determine the evolutionary development of the protein represented by the probe. Similarly, the microarray can be constructed of multiple tissue types from a single species, or from different developmental stages of a single species (or multiple species) thus simply and efficiently determining tissue expression of the protein represented by the probe. For example, a microarray can be constructed with arrayed samples representing all the developmental stages of *Drosophila*, a well known organism the study of which has led to a greater understanding of mammalian physiology and development.

The nucleic acid sample can be messenger ribonucleic acid (mRNA) or can be complementary deoxyribonucleic acid (cDNA), including EST fragments. Methods for extracting and isolating nucleic acids from cells are well known in the art (for example phenol extraction/ethanol precipitation, ammonium acetate precipitation, cesium chloride gradients, and the like), as are methods for generating cDNA (see, for example, "Molecular Cloning: A Laboratory Manual," second edition, edited by Sambrook, Fritsch, & Maniatis, Cold Spring Harbor Laboratory, 1989; and Ausubel, et al, Short Protocols in Molecular Biology, 3rd ed. 1995, both of which are incorporated by reference herein). Microarrays of these nucleic acids are created using the methods described above. Techniques for coupling nucleic acids to solid supports used to construct microarrays are well known in the art, including the poly-L-lysine and phenylboronic acid methods described in the Examples below.

The nucleic acid probes used in the invention methods can be designed based on the sequence of a gene encoding a known protein or can be an EST fragment, as described above. One skilled in the art can readily design such probes based on the known sequence using methods of computer alignment and sequence analysis known in the art (e.g., "Molecular Cloning: A Laboratory Manual", second edition, edited by Sambrook, Fritsch, & Maniatis, Cold Spring Harbor Laboratory, 1989; Ausubel, et al, Short Protocols in Molecular Biology, 3rd ed. 1995). The probe can comprise any number of nucleotides but will preferably be not fewer than 10 nucleotides and preferably not more than about 300 nucleotides in length.

The probes of the invention can be labeled by standard labeling techniques such as with a radiolabel, enzyme label, fluorescent label, biotin-avidin label, chemiluminescent label, and the like. After hybridization, the probes may be detected using known methods. Preferred labels are fluorescent labels, as described above.

The nucleic acid probes of the present invention include RNA as well as DNA probes and nucleic acids modified in the sugar, phosphate or even the base portion as long as the probe still retains the ability to specifically hybridize under conditions as disclosed herein. Such probes are generated using techniques known in the art.

The term "hybridize" as used herein refers to a method of interacting a nucleic acid sequence with a DNA or RNA molecule in solution or on a solid support, such as cellulose or nitrocellulose. If a nucleic acid sequence binds to the DNA or RNA molecule with sufficiently high affinity, it is said to "hybridize" to the DNA or RNA molecule. The strength of the interaction between the probing sequence and its target can be assessed by varying the stringency of the hybridization conditions. Various low to high stringency hybridization conditions may be used depending upon the specificity and selectivity desired. Stringency is controlled by varying salt or denaturant concentrations. Examples of hybridization conditions are shown in the Examples below. Those skilled in the art readily recognize how such conditions can be varied to vary specificity and selectivity. For example, under highly stringent hybridization conditions only highly complementary nucleic acid sequences hybridize. Preferably, such conditions prevent hybridization of nucleic acids having even one or two mismatches out of 20 contiguous nucleotides.

In a further aspect of the invention, microarrays can be composed of randomly generated polynucleotides (DNA or RNA) and contacted with proteins to identify unique binding pairs. Polynucleotides are now known to bind to proteins and may have potential as diagnostics and therapeutics (see, for example, Allen, et al, Virology 209(2):327-336, 1995; Binkley, et al, Nucleic Acids Res. 23(16):3198-3205, 1995). Polynucleotides can be evaluated in very large numbers using the methods disclosed herein thus increasing the likelihood of identifying a useful binder.

The invention will now be described in greater detail by reference to the following non-limiting examples.

EXAMPLES

Example 1

Nucleic Acid Microarrays

The following procedures are conducted at room temperature and using double distilled water unless otherwise noted. These methods are applicable to arrays of polypeptides or polynucleic acids.

Glass slides are prepared as follows: NaOH (50 g) is dissolved in 150 ml of double distilled water ($ddH_2O$), then 200 ml of 95% EtOH is added while stirring. If the solution becomes cloudy, $ddH_2O$ is added until it becomes clear. Approximately 30 glass slides (Gold Seal, Cat. No. 3010) are soaked in the NaOH/EtOH solution for 2 hours, shaking. The slides are then rinsed three times with $ddH_2O$. The slides are next soaked in a poly-L-lysine solution (70 ml poly-L-lysine (Sigma Cat. No. 8920) to 280 $ddH_2O$) for 1 hour. Excess liquid is removed by spinning the slides in a rack on a microtiter plate carrier at 500 rpm. The slides are dried at 40° C. for 5 minutes, then stored in a closed box for at least 2 weeks prior to use.

A cDNA microarray is prepared as follows: Total mRNA is isolated from tissue (for example, nerve cells) of a variety of species representative of different classes of organisms such as *Drosophila*, nematode, salmon, clam, chicken, mouse, dog, goat, spider monkey, chimpanzee, human, and the like, by the FastTrac method (Stratagene, La Jolla, Calif.) or other common methods. mRNA is also obtained from a variety of unicellular organisms such as *E. coli*, yeast, *B. subtilis*, mycoplasma and the like. Eukaryotic mRNA is enriched from total RNA using oligo(dT) cellulose (Ausubel, et al, Short Protocols in Molecular Biology, 3rd ed. 1995, pgs 4-11-4-12). Equivalent amounts (for example, 1 µg) of mRNA from each source are placed in a separate well of one or more 96 well microtiter plates and precipitated with cold EtOH. The precipitate is rinsed with 70% EtOH and allowed to dry.

The dried mRNA is resuspended in 3×SSC (sodium chloride/sodium citrate-20× solution is 3 M NaCl (175 g/L 0.3 M trisodium citrate 2H$_2$O (88 g/L adjusted to pH 7.0 with 1 M HCl) then spotted onto a previously prepared glass slide using an array device (for example, Shalon and Brown (WO 95/35505, published Dec. 28, 1995)). The prepared array can be kept for a long period of time before probing, however, if the slides are to be kept for long periods of time, stability is increased by converting each mRNA sample into cDNA using techniques known in the art, such as PCR.

The array is rehydrated by suspending the slide over a dish of ddH$_2$O (50° C.) for approximately one minute. The slide is quickly (approximately 3 seconds) dried by placing it on a surface heated to 100° C. (mRNA side up). The mRNA is crosslinked to the poly-L-lysine coating of the slide using ultraviolet radiation using a Stratalinker™ UV device according to the manufacturer's instructions (Stratagene) set at 60 milliJoules.

The slides are next soaked in a solution of 5 grams of succinic anhydride (Aldrich Cat. No. 23, 969-0) dissolved in 315 ml of N-methyl-pyrrilidinone (Aldrich Cat. No. 32,863-4) plus 35 mls of 0.2 M sodium borate (brought to pH 8.0 with NaOH) for 15 minutes with shaking. The slide is then transferred to a 95° C. water bath for 2 minutes followed by 95% EtOH for 1 minute. Excess liquid is removed from the slides by spinning a rack of slides on a microtiter plate carrier at 500 rpm.

A probe sequence of a known protein (for example, human nerve growth factor, GenBank Accession No. E03589) is labeled using standard protocols, for example by using a CyDye™ Nick Translation kit (Amersham). The labeled probe (approximately 1 µg/ml) is resuspended in 4×SSC (10 µl) to which is added 0.2 µl 10% sodium dodecyl sulfate (SDS). The probe is boiled for 2 minutes, then cooled for 10 seconds and transferred to the array by pipette. The array is covered by a 22 mm×22 mm cover slip, and the slide is placed in a humid hybridization chamber and submerged into a hot water bath (>75° C.).

The slide is left in the bath for 10-24 hours, then the cover slip is removed and the slide rinsed in 0.2×SSC with 0.1% SDS several times. Excess wash buffer is removed by centrifugation on a microtiter plate carrier as described above. The slide is scanned using a spectrofluorometer, such as the ScanArray 3000 (General Scanning Inc., Watertown, Mass.). For probes labeled with Cy5, for example, fluorescence is measured at 670 nm. Localization of spots on the array to which the probe hybridizes indicates that the species represented by the spot expresses a protein similar or identical to the probe protein.

The procedure outlined below is an alternative method for binding arrayed molecules to a solid support, using an SA(OCH$_2$CN)—X—NHS linkage (see, for example, U.S. Pat. No. 5,594,111, issued Jan. 14, 1997; U.S. Pat. No. 5,648, 470, issued May 15, 1997; U.S. Pat. No. 5,623,055, issued Apr. 22, 1997; all of which are incorporated by reference herein).

Glass slides (Fisher Catalog No. 12-544-4) are soaked in an acid bath (1 hour in 0.1 M HCl), then washed with water and dried at room temperature. The slides should not be aggressively dried, such as in an oven. The slides are next soaked in a silane solution overnight at room temperature (5% APTES (3-aminopropyl-triethoxysilane, Aldrich 28, 177-8), 0.3% DIEA (Sigma) v/v in EtOH). The slides may be sonicated for 10-15 minutes right after being placed in the APTES solution.

The slides are rinsed with isopropyl alcohol, then sonicated in isopropyl alcohol for several minutes. Sonication should remove any white silane residue on the slides. If the residue remains, the slides should be discarded. After sonication, the slides are left to cure/dry for at least 24 hours before use.

The cured slides are next soaked in a linker solution overnight at room temperature. The linker solution is made by dissolving 115 mg of 9Y SA(OCH$_2$CN)—X—COOH (Prolix, Bothell, Wash.) in 1 ml dimethylformamide (DMF) plus 60 µl DIEA, then adding 60 mg TSTU (Sigma) and leaving for 15 minutes at room temperature. This stock is diluted in 270 ml of isopropyl alcohol plus 270 µl DIEA before using.

The slides are removed from the linker solution and soaked in 1 M NH$_2$OH, 1 mM EDTA, 0.1 M NaHCO$_3$ (pH 10) for 4 hours at room temperature. This solution is removed, the slides are extensively washed with water then let air dry at room temperature. The slides can be stored at room temperature away from light before using to make arrays.

Example II

Determination of Optimal Concentrations of Antibody and Antigen

Various concentrations (1 µg/µl, 100 ng/µl, 10 ng/µl, 1 ng/µl) of total mouse IgG or a mouse monoclonal anti-PLC-gamma were spotted on aldehyde slides (Cel Associates, Inc., Houston, Tex.), which allow non-covalent attachment of proteins. Using a manual 8 pin hand arrayer the slides were blocked for 1 hour with PBST (phosphate buffered saline and 0.10% Tween 20), and 3% milk protein. The slides were subsequently washed three times, 15 minutes each, in PBST. Duplicate slides were incubated with 50 µl of goat anti-mouse IgG antibody (GAMG) conjugated with CY3 or CY5 fluorescent dye compounds (Amersham, Arlington Heights, Ill.) at 10 µg/ml or 1 µg/ml. Slides were then washed for 15 minutes in PBST three additional times and dried by centrifugation prior to scanning. Binding was detected as shown in Table 1 below.

Example III

Comparison of Solid Supports

Serial dilutions (1 µg/ml, 100 ng/ml, 10 ng/ml, 1 ng/ml) of mouse IgG or PLC-gamma were hand arrayed onto aldehyde, polystyrene, nitrocellulose and Surmodics slides. Aldehyde, nitrocellulose, polystyrene and Surmodics slides were purchased from various outside vendors (aldehyde Slides—Cel Associates, Inc., Houston, Tex.; nitrocellulose Slides—Molecular Probes, Inc., Eugene, Oreg.; polystyrene Slides-Nunc, Inc., Naperville, Ill.; Surmodics Slides—Surmodics, Inc., Eden Prairie, Minn.). Surmodics slides have an undisclosed polymer on the glass surface which forms a covalent linkage with proteins under the appropriate conditions (described by the manufacturer).

Following hand arraying of the antibodies (approximately 20-30 nanoliters per spot), the nitrocellulose, aldehyde, and polystyrene slides were immediately blocked for 1 hour with PBST and 3% milk, washed 3 times with PBST, and hybridized with 50 μl of GAMG-CY3 for 30 minutes. Surmodics slides were incubated overnight in a moist salt chamber as recommended by the manufacturer. The following day, the Surmodics slides were processed as described above. Following hybridization all of the various slides were washed 3 times in PBST, dried and scanned using a Scan Array 3000 fluorescent scanner.

TABLE 1

| Antibody | Conc. | Antigen | Conc. | Detection Level |
|---|---|---|---|---|
| PLC-gamma | 1 μg/μl | GAMG-CY3 | 10 μg/ml | +++ |
|  | 100 ng/μl |  | 10 μg/ml | +++ |
|  | 10 ng/μl |  | 10 μg/ml | + |
|  | 1 ng/μl |  | 10 μg/ml | − |
| mouse IgG | 1 μg/μl | GAMG-CY3 | 10 μg/ml | +++ |
|  | 100 ng/μl |  | 10 μg/ml | +++ |
|  | 10 ng/μl |  | 10 μg/ml | + |
|  | 1 ng/μl |  | 10 μg/ml | − |
| PLC-gamma | 1 μg/μl | GAMG-CY3 | 1 μg/ml | + |
|  | 100 ng/μl |  | 1 μg/ml | + |
|  | 10 ng/μl |  | 1 μg/ml | − |
|  | 1 ng/μl |  | 1 μg/ml | − |
| mouse IgG | 1 μg/μl | GAMG-CY3 | 1 μg/ml | + |
|  | 100 ng/μl |  | 1 μg/ml | + |
|  | 10 ng/μl |  | 1 μg/ml | − |
|  | 1 ng/μl |  | 1 μg/ml | − |
| PLC-gamma | 1 μg/μl | GAMG-CY5 | 10 μg/ml | +++ |
|  | 100 ng/μl |  | 10 μg/ml | +++ |
|  | 10 ng/μl |  | 10 μg/ml | + |
|  | 1 ng/μl |  | 10 μg/ml | − |
| mouse IgG | 1 μg/μl | GAMG-CY5 | 10 μg/ml | +++ |
|  | 100 ng/μl |  | 10 μg/ml | +++ |
|  | 10 ng/μl |  | 10 μg/ml | + |
|  | 1 ng/μl |  | 10 μg/ml | − |
| PLC-gamma | 1 μg/μl | GAMG-CY5 | 1 μg/ml | + |
|  | 100 ng/μl |  | 1 μg/ml | + |
|  | 10 ng/μl |  | 1 μg/ml | − |
|  | 1 ng/μl |  | 1 μg/ml | − |
| mouse IgG | 1 μg/μl | GAMG-CY5 | 1 μg/ml | + |
|  | 100 ng/μl |  | 1 μg/ml | + |
|  | 10 ng/μl |  | 1 μg/ml | − |
|  | 1 ng/μl |  | 1 μg/ml | − |

+++ strong signal,
++ moderate signal
+ weak signal,
− no signal

All of the slides tested allowed for the detection of antigen: antibody binding at higher concentrations of antibody. The Aldehyde and Nitrocellulose treated slides were the most efficient at binding antibody, and antibody:antigen interaction could be detected at 1 ng/μl.

Example IV

Detection of Binding Using Non-Fluorescent Methods

Positively charged nylon filters (Zeta Probe Membranes, BioRad Laboratories, Hercules, Calif.) were hand arrayed using 1 μl of anti-His, anti-V5, anti-thioredoxin (anti-Thio), anti-FOS, anti-PLC-gamma and anti-CREB antibodies (Invitrogen, Carlsbad, Calif.; all antibodies were approximately 1 mg/ml). Filters were blocked for 1 hour with PBST and 3% milk, washed three times with PBST, and incubated with 1 μg/ml biotinylated D1 protein for three hours at room temperature. D1 is a creatine kinase fusion protein isolated from a human fetal heart cDNA library and cloned into the pBAD-Thio-His-TOPO vector (Invitrogen, Carlsbad, Calif.) to create a Thioredoxin-V5-His-creatine kinase fusion protein. D1 was biotinylated using the EZ-Link™ Sulfo-NHS-LC Biotinylation Kit (Pierce, Rockford, Ill.) used according to the manufacturer's instructions).

Following three additional washes with the same buffer, filters were treated with streptavidin/alkaline phosphatase conjugate or streptavidin/horseradish peroxidase conjugate (Boehringer Mannheim, GmbH Germany) for 1 hour at room temperature.

The filters were washed 5 times with PBST, dried, and developed by immersion in ECL chemiluminescent substrate (ECL—Amersham, Arlington Heights, Ill.) or the chromogenic substrate BCIP/NBT (Sigma Chemicals, St. Louis, Mo.). Filters developed with ECL were exposed to Kodak chemiluminescent film for 1 to 10 seconds.

Figure 1B:
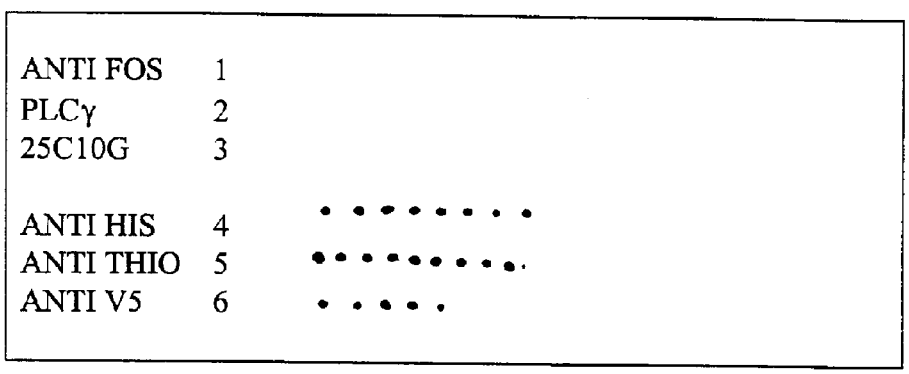
Figure 1C:
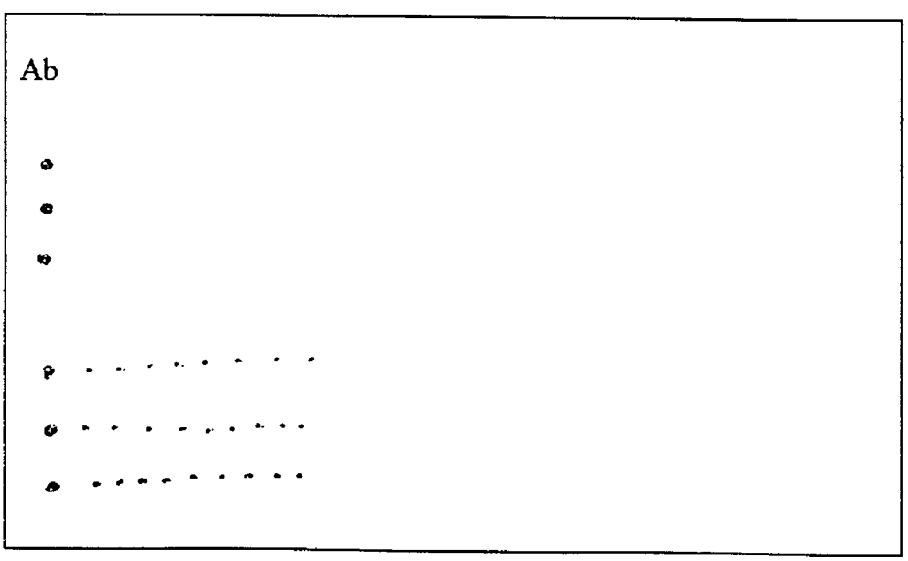

The results are shown in FIGS. 1A, 1B, and 1C. In all cases, only the antibodies specific for epitopes on the fusion protein antigen were detectable, and only in the arrayed spots, showing that the system has both good signal to noise ratio and specificity.

The experiment was repeated using an array created with an automated arrayer. Antibodies (1 mg/ml) were spotted using an automated 96 pin microarrayer developed at Invitrogen. Fifteen negative control antibodies (assorted mouse monoclonals) were arrayed along with the three positive control antibodies (anti-His, anti-Thio, anti-V5). Filters were treated as described above using the alkaline phosphatase conjugate and the chromogenic substrate BCIP/NBT.

Figure 2:
FIG. 2 shows a microarray produced using a robotic arraying apparatus. Antigen binding is detected by non-fluorescent means.

As can been seen in FIG. 2, binding and detection of antibody:antigen complexes was highly specific and sensitive.

Example V

Evaluation of Antibody Affinity

Figure 3:
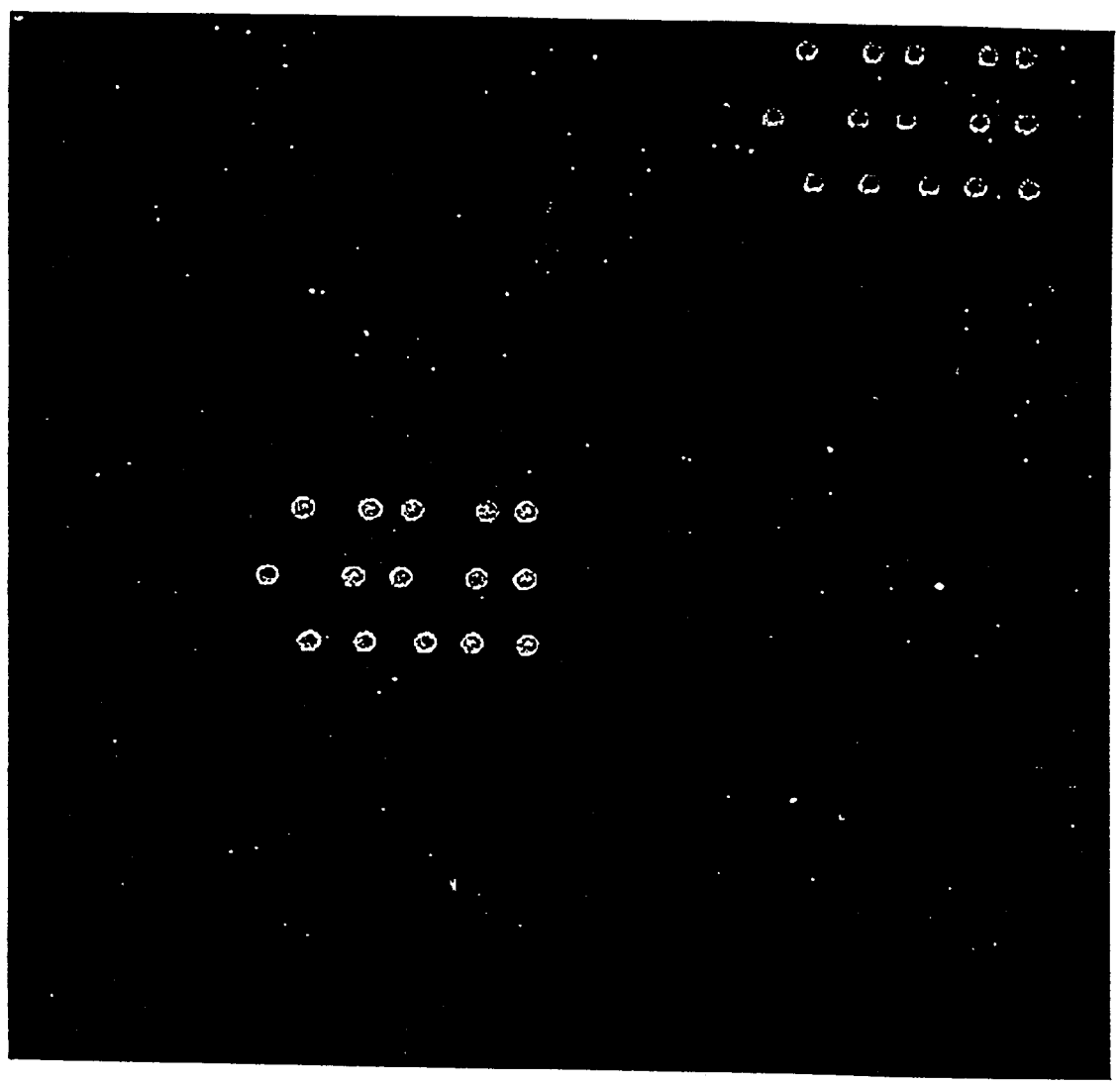
FIG. 3 shows the ability of the antibody microarrays to evaluate relative binding affinities to a specific antigen.

Anti-His, anti-V5, anti-FOS, anti-PLC-gamma, 25C1DG, and anti-VEGF (vascular endothelial growth factor) antibodies were arrayed on a nitrocellulose slide and reacted with biotinylated D1 protein as previously described. Binding was detected with streptavidin-Cy3 as described above. The anti-V5 antibodies spots showed red, the anti-His spots showed green, while the negative controls were undetectable (see FIG. 3). When viewed in a black and white drawing, relative increase in binding affinity is visualized by an increase of white in a given area. The color of the spots generally indicates a higher amount of fluorescently labeled antigen present, and thus indicates relative binding affinity between antibody and antigen. Colors, in descending order from highest to lowest affinity, are white, red, yellow, green, and blue. Using this technique, multiple antibodies can be tested for their affinity to a single antigen.

Example VI

Polyclonal Antibody Microarrays

To demonstrate specific binding to polyclonal antibodies, six antibodies were arrayed by hand on a nitrocellulose slide, three polyclonal antibodies (anti-E12 (unpurified rabbit polyclonal sera to a His-V5-thioredoxin-thymidine kinase fusion protein), anti-lexA (lexA repressor protein), and anti-GFP (Green fluorescent protein)) and three monoclonal antibodies (anti-V5, anti-His and anti-GalU (a mammalian transcription factor). The slide was blocked with PBST and 3% milk for 1 hour at room temperature, and incubated with the E12-biotin conjugate, prepared according to the protocol used for D1 protein. Following extensive washing with PBST, the slides were incubated with streptavidin-CY3 conjugate (Amersham, Arlington Heights, Ill.) for 1 hour at room temperature, washed 5 times with PBST and dried by centrifugation prior to scanning on the Scan Array 3000.

Figure 4:
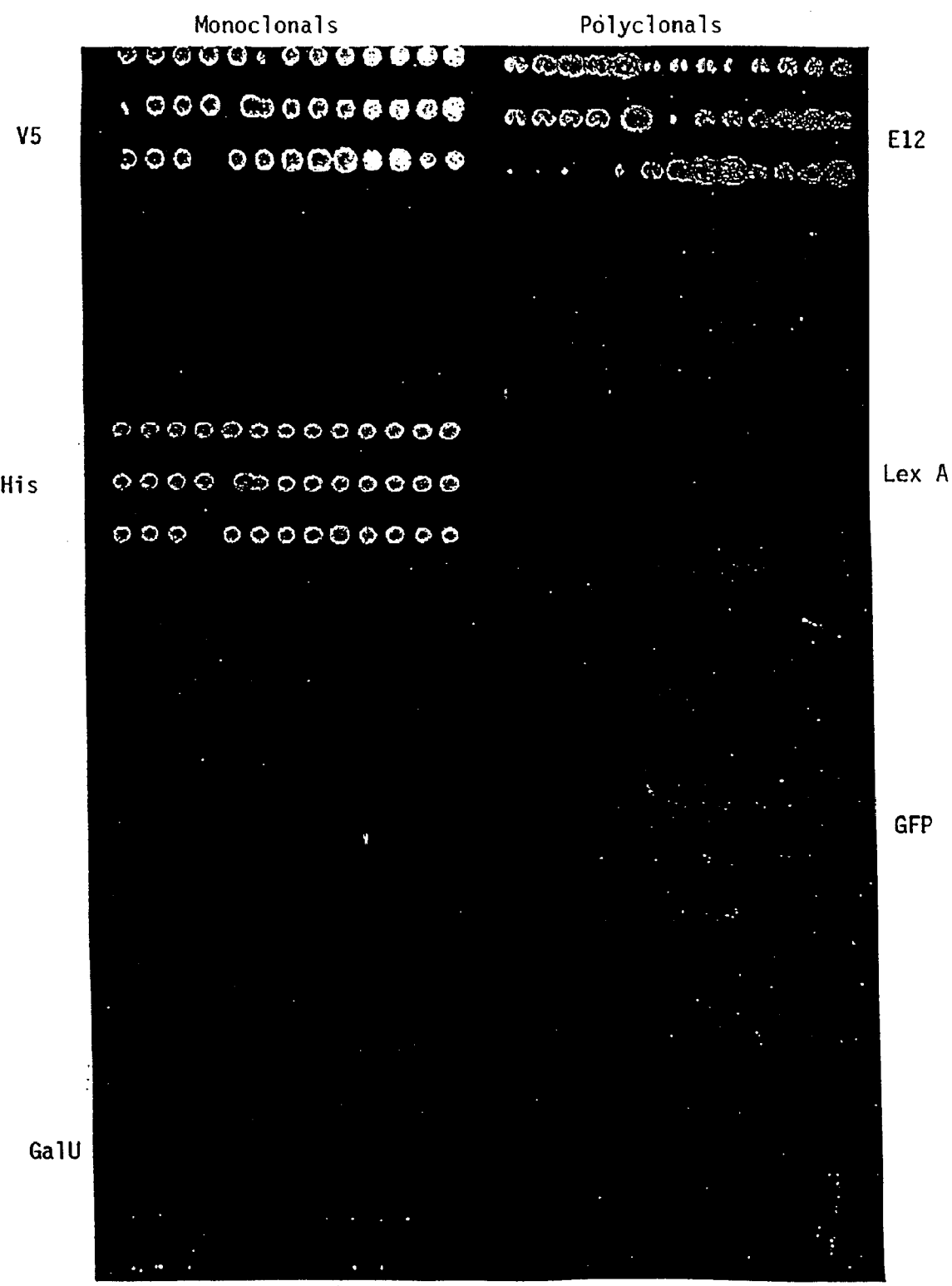
FIG. 4 shows a microarray of polyclonal antibodies in comparison to a microarray of monoclonal antibodies.

As can be seen in FIG. 4, binding was detected with both the antigen specific polyclonal antibody (anti-E12) and the antigen specific monoclonal antibodies (anti-His, anti-V5) and not with any of the negative control antibodies.

Example VII

Microarray Analysis of Labeled Cell Lysate

A series of experiments were conducted to determine if a microarray of antibodies could specifically detect antigens in a cell lysate.

CHO cells expressing high levels of beta-galactosidase were grown to confluency in a T-175 flask. (Hams media with Pen/Strep, and L-glutamine plus 10% FCS, at 37° C. with 5% $CO_2$) Cells were harvested using Trypsin/EDTA. NP40 extracts were prepared by pelleting the cells ($10^7$ cells), washing once in PBS and resuspending in 5% NP40. Cell debris was removed by centrifugation. Soluble protein was biotinylated using a Pierce biotinylation kit according to the manufacturer's instructions.

Figure 5A:
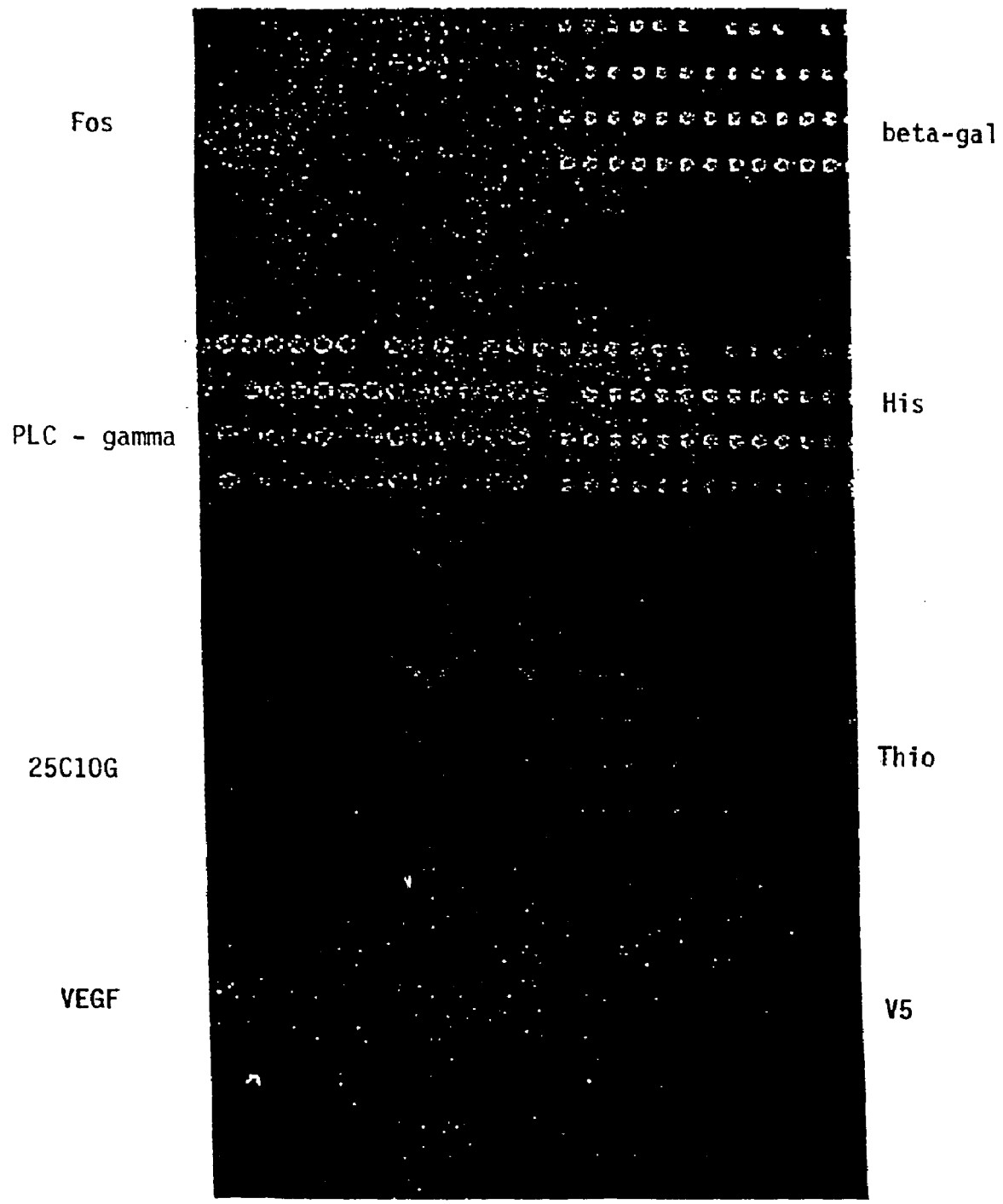
FIGS. 5A, 5B and 5C show a microarray of antibodies reacted with a cell lysate under conditions that vary the amount of background binding.

Nitrocellulose slides (see above) containing arrayed monoclonal antibodies (anti-beta-gal, anti-His, anti-Thio, anti-V5, anti-FOS, anti-PLC-gamma, anti-VEGF and 25C 10G (an anti-CREB antibody) were blocked, washed, hybridized and developed with streptavidin-CY3 as described in Example VI supra. As can be seen in FIG. 5A, beta-galactosidase binding was seen, however, some non-specific binding was detected as well.

Figure 5B:
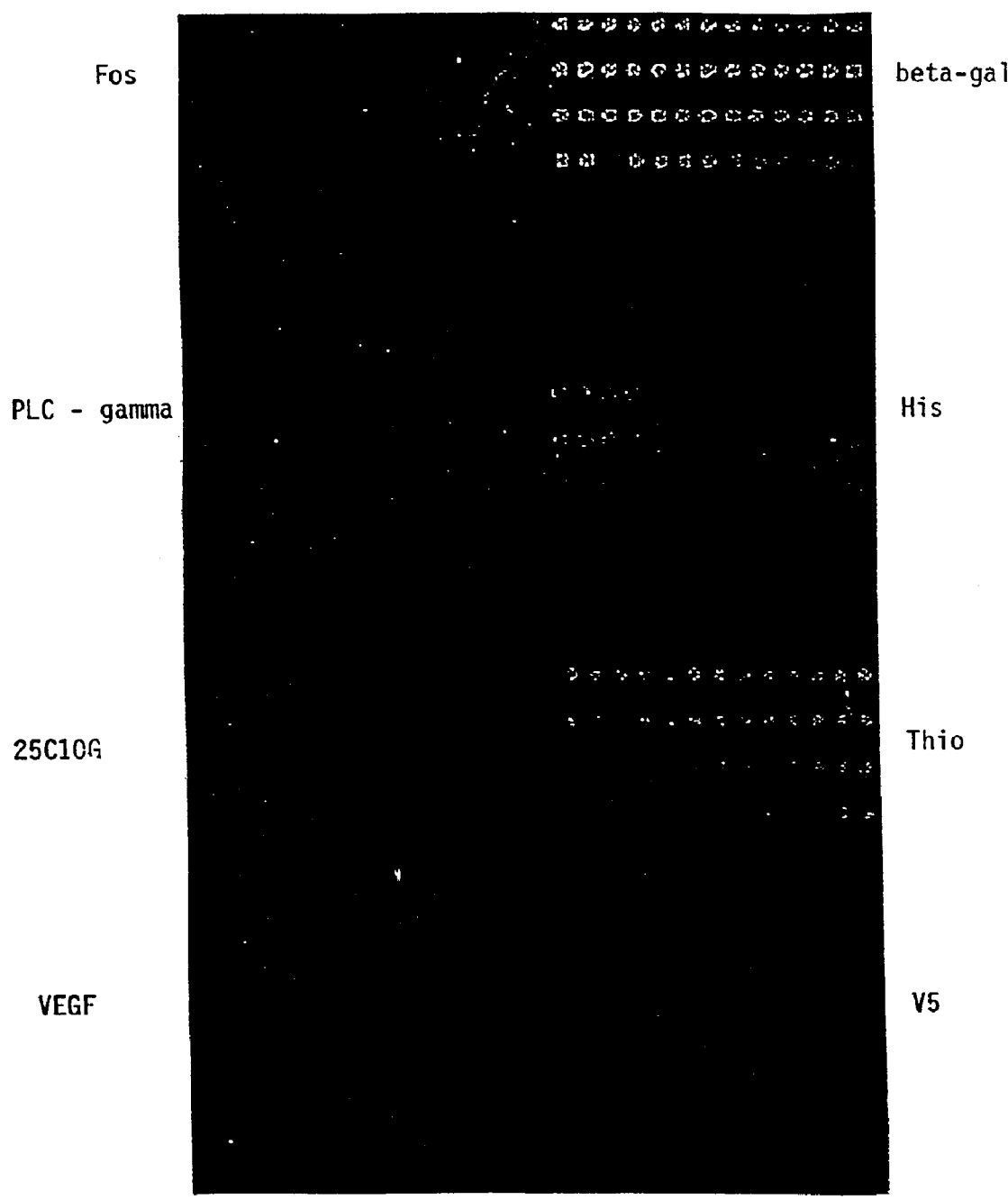

The experiment was repeated, except that after centrifugation of the extract, soluble protein was dialyzed overnight against 50 mM phosphate buffer at 4° C. prior to biotinylation. As can be seen in FIG. 5B, much of the non-specific binding seen in the previous experiment was eliminated.

Figure 5C:
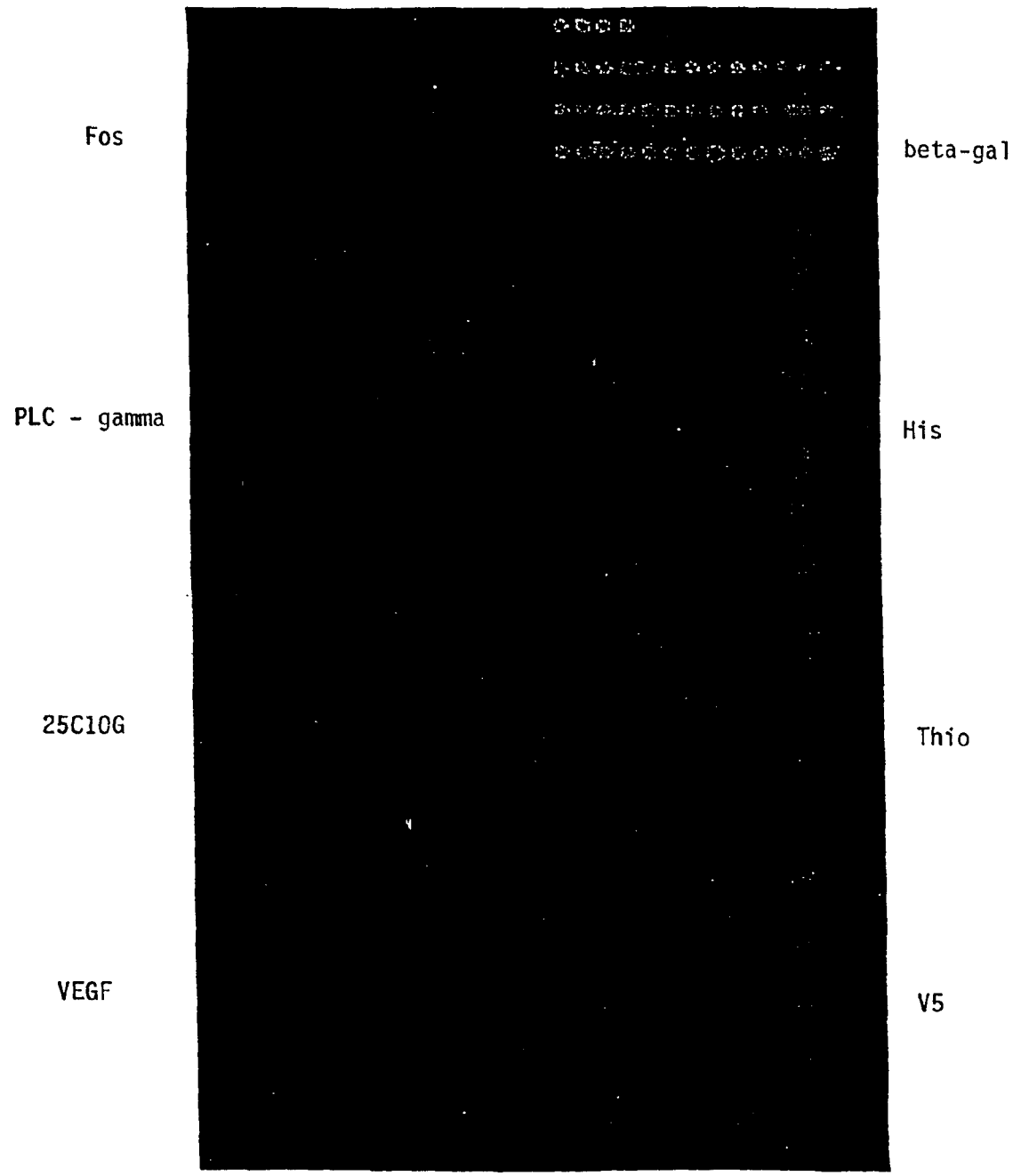

In the next experiment dialyzed extract containing the biotinylated soluble proteins was adjusted to 10% glycerol to reduce non-specific hydrophobic interactions. Furthermore, the sodium chloride concentration was adjusted to 0.2 M NaCl to increase specific ionic interactions. All other conditions remained identical. As can be seen in FIG. 5C, all non-specific binding was eliminated using this protocol.

While the foregoing has been presented with reference to particular embodiments of the invention, it will be appreciated by those skilled in the art that changes in these embodiments may be made without departing from the principles and spirit of the invention, the scope of which is defined by the appended claims.

That which is claimed is:

1. A method of comparing protein expression in two or more populations of cells, said method comprising:
    (a) contacting an array of antibodies bound to a solid surface with a cell lysate of a first cell population, generating a first binding pattern;
    (b) contacting a duplicate array of antibodies on a solid surface with a cell lysate of a second cell population, generating a second binding pattern; and
    (c) comparing the binding pattern of the first cell lysate with the binding pattern of the second cell lysate.

2. The method according to claim 1, wherein the antibodies are of uncharacterized binding specificity.

3. The method according to claim 1, wherein the antibodies are recombinant antibodies.

4. The according to claim 1, wherein the first cell lysate is derived from normal cells and the second cell lysate is derived from abnormal cells.

5. The method according to claim 4, wherein the abnormal cells are cancer cells.

6. The method according to claim 1, wherein the first cell lysate is derived from cells in a resting state and the second cell lysate is derived from cells in a stimulated state.

7. The method according to claim 1, wherein at least one of the one of the two cell lysates comprises a detectable label.

8. The method according to claim 1, wherein each of the two cell lysates comprises a different detectable label.

9. A method of comparing protein expression in two or more protein samples, said method comprising:
    (a) contacting an array of antibodies bound to a solid surface with a first protein sample, generating a first binding pattern;
    (b) contacting a duplicate array of antibodies on a solid surface with a second protein sample, generating a second binding pattern; and
    (c) comparing the binding pattern of the first protein sample with the binding pattern of the second protein sample.

10. The method according to claim 9, wherein the first and second protein samples are derived from a body fluid.

11. The method according to claim 9, wherein the first and second protein samples are derived from serum samples.

12. The method according to claim 9, wherein the first and second protein samples are derived from cerebral spinal fluid, blood, plasma, urine, feces, saliva, tears, or extracted tissue.

13. The method according to claim 9, wherein the first and second protein samples are derived from cellular extracts.

* * * * *